United States Patent
Dollings

(10) Patent No.: US 6,258,784 B1
(45) Date of Patent: Jul. 10, 2001

(54) ACETAL BENZYLMALTOSIDES AS INHIBITORS OF SMOOTH MUSCLE CELL PROLIFERATION

(75) Inventor: Paul J. Dollings, Newtown, PA (US)

(73) Assignee: American Home Products Corp., Madison, NJ (US)

(*) Notice: Subject to any disclaimer, the term of this patent is extended or adjusted under 35 U.S.C. 154(b) by 0 days.

(21) Appl. No.: 09/444,077

(22) Filed: Nov. 22, 1999

Related U.S. Application Data

(60) Provisional application No. 60/126,432, filed on Nov. 24, 1998.

(51) Int. Cl.[7] ................ A61K 31/7008; A61K 31/7016; A61K 31/7028; C07H 3/04; C07H 5/00
(52) U.S. Cl. .............................. 514/24; 514/25; 514/53; 536/4.1; 536/17.2; 536/17.5; 536/17.6; 536/22.1; 536/123.13
(58) Field of Search .................. 514/24, 25, 53; 536/4.1, 17.2–17.9, 22.1, 29.2, 123.13

(56) References Cited

U.S. PATENT DOCUMENTS

| | | | |
|---|---|---|---|
| 2,752,334 | 6/1956 | Walton | 260/211 |
| 4,431,637 | 2/1984 | Upeslacis et al. | 424/180 |
| 5,019,562 | 5/1991 | Folkman et al. | 514/58 |
| 5,037,973 | 8/1991 | Meinetsberger | 536/53 |
| 5,296,588 | 3/1994 | Au et al. | 536/1.11 |
| 5,310,542 | 5/1994 | Au et al. | 424/52 |
| 5,336,765 | 8/1994 | Au et al. | 536/18.5 |
| 5,464,827 | 11/1995 | Soll | 514/58 |
| 5,498,775 | 3/1996 | Novak et al. | 514/25 |
| 5,773,420 | * 6/1998 | Nguyen et al. | 514/25 |

FOREIGN PATENT DOCUMENTS

| | | |
|---|---|---|
| 0312086 | 4/1989 | (EP) . |
| 0312087 | 4/1989 | (EP) . |
| 0356275 | 2/1990 | (EP) . |
| 0454220 | 10/1991 | (EP) . |
| 0550106 | 7/1993 | (EP) . |
| 0551675 | 7/1993 | (EP) . |
| 9006755 | 6/1990 | (WO) . |
| 9309790 | 5/1993 | (WO) . |
| 9614324 | 5/1996 | (WO) . |
| 9614325 | 5/1996 | (WO) . |

OTHER PUBLICATIONS

Zehavi, Carbohyd. Res., 1986, 151, 371.
Reilly et al., Drug Development Research, 1993, 29, 137.
Klein et al., Liebigs Ann. Chem., 1987, 485–489.
Durette et al., Carbohydrate Research, 1978, 67, 484–490.
Bertho, Liebigs Ann. Chem., 1949, 562, 229–239.
Kopper et al., Carbohydrate Research, 1989, 193, 296–302.
Zehavi et al., Carbohydrate Research, 1983, 124, 23–34.
Zehavi et al., Carbohydrate Research, 1992, 228, 255–263.
Connors et al., Herba Polonica, 1998, 44, 33–38.
Morales et al., Angew. Chem. Int. Ed, 1988, 37 (5), 654–657.

* cited by examiner

Primary Examiner—Gary Geist
Assistant Examiner—Leigh C. Maier
(74) Attorney, Agent, or Firm—Michael R. Nagy

(57) ABSTRACT

This invention provides smooth muscle cell proliferation inhibitors of formula I having the structure

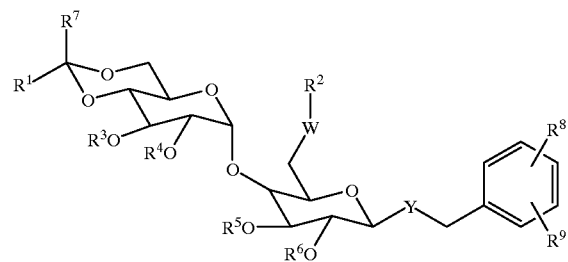

I wherein

W is S, SO, $SO_2$, NR;

Y is O, S, NR, or $CH_2$;

R is hydrogen or alkyl of 1–6 carbon atoms, perfluoroalkyl of 1–6 carbon atoms, acyl of 2–7 carbon atoms, perfluoroacyl of 2–7 carbon atoms;

$R^1$ and $R^7$ are each, independently, alkyl of 1–6 carbon atoms, perfluoroalkyl of 1–6 carbon atoms, haloalkyl of 1–6 carbon atoms, nitroalkyl of 1–6 carbon atoms, cyanoalkyl of 1–6 carbon atoms, alkoxyalkyl of 2–12 carbon atoms, nitriloalkyl of 1–6 carbon atoms, phenyl mono-, di-, or tri-substituted with $R^8$, phenylalkyl of 7–10 carbon atoms, wherein the phenyl ring is mono-, di-, or tri-substituted with $R^8$, pyridyl substituted with $R^8$, furyl substituted with $R^8$, thienyl substituted with $R^8$, and thiazolyl substituted with $R^8$;

$R^2$ is hydrogen,

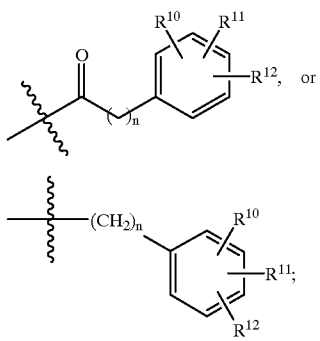

$R^3$, $R^4$, $R^5$, and $R^6$ are each, independently, hydrogen, acyl of 2–7 carbon atoms, perfluoroacyl of 2–7 carbon atoms, alkyl of 1–6 carbon atoms, perfluoroalkyl of 1–6 carbon atoms, benzyl, wherein the phenyl moiety is mono-, di-, or tri-substituted with $R^8$, benzoyl, wherein the phenyl moiety is mono-, di-, or tri-substituted with $R^8$;

$R^8$ is hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —$NO_2$, halogen, or —$CF_3$;

$R^9$ is hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —$NO_2$, halogen, —$NHCO_2R^{13}$, —$NHSO_2R^{13}$, —$NR^{14}R^{15}$,

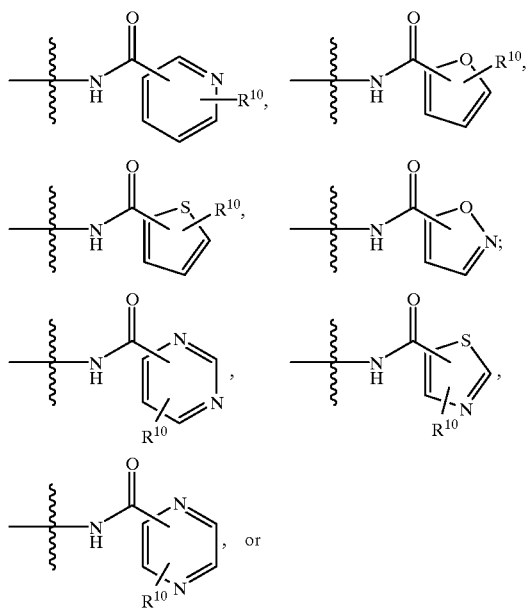

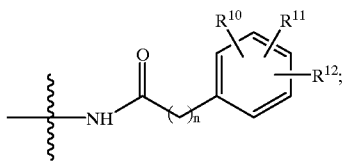

-continued $R^{10}$, $R^{11}$, and $R^{12}$, are each, independently, hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —$NO_2$, halogen, acyl of 2–7 carbon atoms, perfluoroacyl of 2–7 carbon atoms, or benzoyl, wherein the phenyl moiety of the benzoyl group is optionally mono-, di-, or tri-substituted with alkyl of 1–6 carbon atoms, alkoxy of 1–6 carbon atoms, —CN, —$NO_2$, halogen, or —$CF_3$;

$R^{13}$ is alkyl of 1–6 carbon atoms, perfluoroalkyl of 1–6 carbon atoms, phenyl or phenyl substituted with halogen;

$R^{14}$ and $R^{15}$ are each, independently, hydrogen, alkyl of 1–6 carbon atoms, perfluoroalkyl of 1–6 carbon atoms, acyl of 2–7 carbon atoms, perfluoroacyl of 2–7 carbon atoms;

n=0–3; or a pharmaceutically acceptable salt thereof.

25 Claims, No Drawings

ACETAL BENZYLMALTOSIDES AS INHIBITORS OF SMOOTH MUSCLE CELL PROLIFERATION

This application claims the benefit of U.S. Provisional Application No. 60/126,432, which was converted from U.S. patent application Ser. No. 09/198,984, filed Nov. 24, 1998, pursuant to a petition filed under 37 C.F.R. 1.53(c)(2)(i).

BACKGROUND OF THE INVENTION

This invention relates to the use of substituted 4',6'-acetal benzylmaltosides as smooth muscle cell proliferation inhibitors and as therapeutic compositions for treating diseases and conditions which are characterized by excessive smooth muscle proliferation such as restenosis.

All forms of vascular reconstruction such as angioplasty and vein bypass procedures effect a response to injury that ultimately leads to smooth muscle cell (SMC) proliferation and subsequently, deposition of profuse amounts of extracellular matrix (Clowes, A. W.; Reidy, M. A. *J. Vasc. Surg* 1991, 13, 885). These events are also central processes in the pathogenesis of atherosclerosis (Raines E. W.; Ross R. *Br. Heart J.* 1993, 69 (Supplement), S. 30) as well as transplant arteriosclerosis (Isik, F. F.; McDonald, T. O.; Ferguson, M.; Yamanaka, E.; Gordon *Am. J. Pathol.* 1992, 141, 1139). In the case of restenosis following angioplasty, clinically relevant solutions for controlling SMC proliferation through pharmacological intervention have remained elusive to date (Herrman, J. P. R.; Hermans, W. R. M.; Vos, J.; Serruys P. *W. Drugs* 1993, 4, 18 and 249). Any successful approach to selective SMC proliferation inhibition must not interfere with endothelial cell repair or the normal proliferation and function of other cells (Weissberg, P. L.; Grainger, D. J.; Shanahan C. M.; Metcalfe, J. C. *Cardiovascular Res.* 1993, 27, 1191).

The glycosaminoglycans heparin and heparan sulfate are endogenous inhibitors of SMC proliferation, yet are able to promote endothelial cell growth (Castellot, J. J. Jr.; Wright, T. C.; Karnovsky, M. J. *Seminars in Thrombosis and Hemostasis* 1987, 13, 489). However, the full clinical benefits of heparin, heparin fragments, chemically modified heparin, low molecular weight heparins, and other heparin mimicking anionic polysaccharides may be compromised due to other pharmacological liabilities (excessive bleeding arising from anticoagulation effects, in particular) coupled with heterogeneity of the various preparations (Borman, S. *Chemical and Engineering News*, Jun. 28, 27, 1993).

WO 96/14325 discloses acylated benzylglycosides as smooth muscle cell proliferation inhibitors. The compounds of the present invention differ in that the substituents on the carbohydrate backbone are different.

Zehavi, U., in *Carbohyd. Res.* 1986, 151, 371, disclosed 4-carboxy-2-nitrobenzyl 4-O-α-D-glucopyranosyl-β-D-glucopyranoside which is attached to a polymer for study as an acceptor in the glycogen synthase reaction. The compounds of the present invention differ in that the substituents on the benzyl groups are different and (c) the use (smooth muscle antiproliferation) is different.

Patent numbers U.S. Pat. No. 5,498,775, WO96/14324, and U.S. Pat. No. 5,464,827 describe polyanionic benzylglycosides or cyclodextrins as smooth muscle cell proliferation inhibitors for treating diseases and conditions which are characterized by excessive smooth muscle proliferation. β-cyclodextrin tetradecasulfate has been described as a smooth muscle cell proliferation inhibitor and as an effective inhibitor of restenosis (Reilly, C. F.; Fujita, T.; McFall, R. C.; Stabilito, I. I.; Wai-se E.; Johnson, R. G. *Drug Development Research* 1993, 29, 137). U.S. Pat. No. 5,019,562 discloses anionic derivatives of cyclodextrins for treating pathological conditions associated with undesirable cell or tissue growth. WO 93/09790 discloses antiproliferative polyanionic derivatives of cyclodextrins bearing at least 2 anionic residues per carbohydrate residues. Meinetsberger (EP 312087 A2 and EP 312086 A2) describes the antithrombotic and anticoagulant properties of sulfated bis-aldonic acid amides. U.S. Pat. No. 4,431,637 discloses polysulfated phenolic glycosides as modulators of the complement system. The compounds of the present invention differ from all of the prior art in that the compounds (a) are 4',6'-acetal benzylmaltosides which bear no structural resemblance to heparin, sulfated cyclodextrins, or to sulfated lactobionic acid dimers, (b) contain no more than two contiguous sugar residues (disaccharide), (c) are of a defined structure, (d) and are not sulfated.

DESCRIPTION OF THE INVENTION

This invention provides 4',6'-acetal benzylmaltosides of formula I

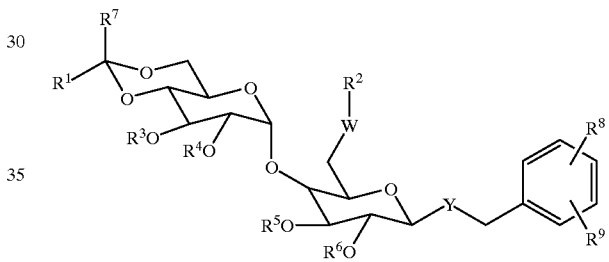

wherein

W is S, SO, SO$_2$, NR;

Y is O, S, NR, or CH$_2$;

R is hydrogen or alkyl of 1–6 carbon atoms, perfluoroalkyl of 1–6 carbon atoms, acyl of 2–7 carbon atoms, perfluoroacyl of 2–7 carbon atoms;

R$^1$ and R$^7$ are each, independently, alkyl of 1–6 carbon atoms, perfluoroalkyl of 1–6 carbon atoms, haloalkyl of 1–6 carbon atoms, nitroalkyl of 1–6 carbon atoms, cyanoalkyl of 1–6 carbon atoms, alkoxyalkyl of 2–12 carbon atoms, 15 nitriloalkyl of 1–6 carbon atoms, phenyl mono-, di-, or tri-substituted with R$^8$, phenylalkyl of 7–10 carbon atoms, wherein the phenyl ring is mono-, di-, or tri-substituted with R$^8$, pyridyl substituted with R$^8$, furyl substituted with R$^8$, thienyl substituted with R$^8$, and thiazolyl substituted with R$^8$;

R$^2$ is hydrogen,

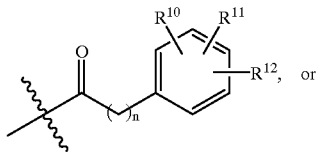

or

-continued

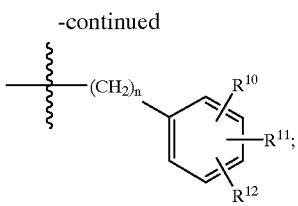

$R^3$, $R^4$, $R^5$, and $R^6$ are each, independently, hydrogen, acyl of 2–7 carbon atoms, perfluoroacyl of 2–7 carbon atoms, alkyl of 1–6 carbon atoms, perfluoroalkyl of 1–6 carbon atoms, benzyl, wherein the phenyl moiety is mono-, di-, or tri-substituted with $R^8$, benzoyl, wherein the phenyl moiety is mono-, di-, or tri-substituted with $R^8$;

$R^8$ is hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —NO$_2$, halogen, or —CF$_3$;

$R^9$ is hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —NO$_2$, halogen, —NHCO$_2R^{13}$, —NHSO$_2R^{13}$, —NR$^{14}$R$^{15}$,

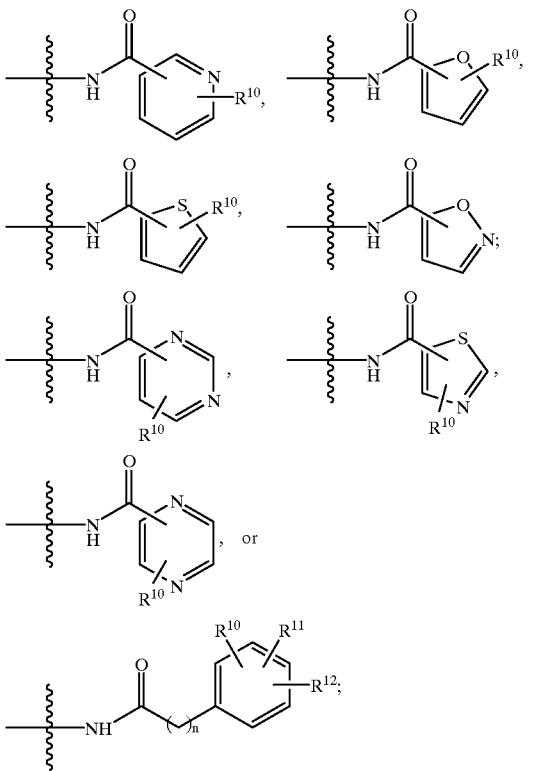

$R^{10}$, $R^{11}$, and $R^{12}$, are each, independently, hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —NO$_2$, halogen, acyl of 2–7 carbon atoms, perfluoroacyl of 2–7 carbon atoms, or benzoyl, wherein the phenyl moiety of the benzoyl group is optionally mono-, di-, or tri-substituted with alkyl of 1–6 carbon atoms, alkoxy of 1–6 carbon atoms, —CN, —NO$_2$, halogen, or —CF$_3$;

$R^{13}$ is alkyl of 1–6 carbon atoms, perfluoroalkyl of 1–6 carbon atoms, phenyl or phenyl substituted with halogen;

$R^{14}$ and $R^{15}$ are each, independently, hydrogen, alkyl of 1–6 carbon atoms, perfluoroalkyl of 1–6 carbon atoms, acyl of 2–7 carbon atoms, perfluoroacyl of 2–7 carbon atoms;

n=0–3;

or a pharmaceutically acceptable salt thereof.

Alkyl, alkoxy and acyl includes both straight chain as well as branched moieties optionally substituted with fluorine. Halogen means bromine, chlorine, fluorine, and iodine.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from organic and inorganic bases, preferably alkali metal salts, for example, sodium, lithium, or potassium. Acid addition salts can be prepared when Y is nitrogen or the compound of formula I contains a basic nitrogen, and base addition salts can typically be prepared when the compound of formula I contains a hydroxyl group.

The compounds of this invention may contain an asymmetric carbon atom or sulfoxide moiety and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

Preferred compounds of this invention are 4',6'-acetal benzylmaltosides of formula I

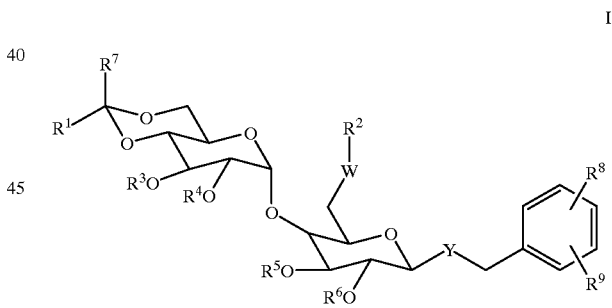

wherein

W is S, SO, SO$_2$, NR;

Y is O;

R is hydrogen or alkyl of 1–6 carbon atoms, perfluoroalkyl of 1–6 carbon atoms, acyl of 2–7 carbon atoms, perfluoroacyl of 2–7 carbon atoms;

$R^1$ is alkyl of 1–6 carbon atoms, perfluoroalkyl of 1–6 carbon atoms, haloalkyl of 1–6 carbon atoms, nitroalkyl of 1–6 carbon atoms, cyanoalkyl of 1–6 carbon atoms, alkoxyalkyl of 2–12 carbon atoms, nitriloalkyl of 1–6 carbon atoms, phenyl mono-, di-, or tri-substituted with $R^8$, phenylalkyl of 7–10 carbon atoms, wherein the phenyl ring is mono-, di-, or tri-substituted with $R^8$, pyridyl substituted with $R^8$, furyl substituted with $R^8$, thienyl substituted with $R^8$, and thiazolyl substituted with $R^8$;

$R^2$ is hydrogen,

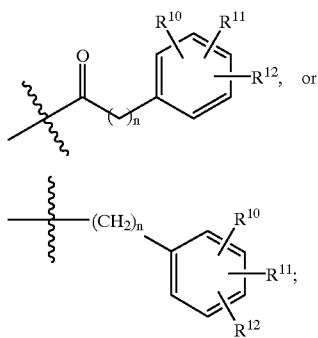

$R^3$, $R^4$, $R^5$, and $R^6$ are each, independently, hydrogen, alkyl of 1–6 carbon atoms, perfluoroalkyl of 1–6 carbon atoms, acyl of 2–7 carbon atoms or perfluoroacyl of 2–7 carbon atoms;

$R^7$ is hydrogen, methyl, or phenyl;

$R^8$ is hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —NO$_2$, halogen, or —CF$_3$;

$R^9$ is hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —NO$_2$, halogen, —NHCO$_2$R$^{13}$, —NHSO$_2$R$^{13}$, —NR$^{14}$R$^{15}$,

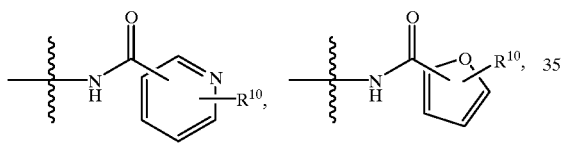

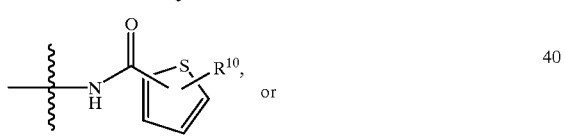

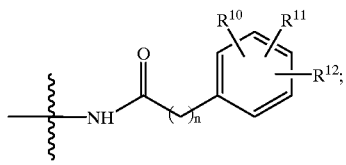

$R^{10}$, $R^{11}$, and $R^{12}$, are each, independently, hydrogen, alkyl of 1–6 carbon atoms, alkoxy of 1–6 carbon atoms, phenyl, —CN, —NO$_2$, halogen, —CF$_3$, acyl of 2–7 carbon atoms, or benzoyl, wherein the phenyl moiety of the benzoyl group is optionally mono-, di-, or tri-substituted with alkyl of 1–6 carbon atoms, alkoxy of 1–6 carbon atoms, —CN, —NO$_2$, halogen, or —CF$_3$;

$R^{13}$ is alkyl of 1–6 carbon atoms, perfluoroalkyl of 1–6 carbon atoms, phenyl or phenyl substituted with halogen;

$R^{14}$ and $R^{15}$ are each, independently, hydrogen, alkyl of 1–6 carbon atoms, perfluoroalkyl of 1–6 carbon atoms, acyl of 2–7 carbon atoms, perfluoroacyl of 2–7 carbon atoms;

n=0–3;

or a pharmaceutically acceptable salt thereof.

More preferred compounds of this invention are benzyl-maltosides of formula

I

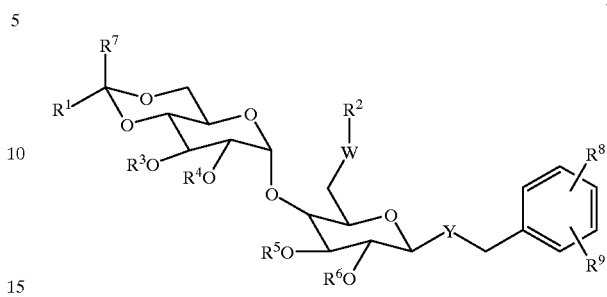

wherein

W is S, SO, SO$_2$, NR;

Y is O;

R is hydrogen or alkyl of 1–6 carbon atoms;

$R^1$ is phenyl mono-, di-, or tri-substituted with $R^8$;

$R^2$ is hydrogen,

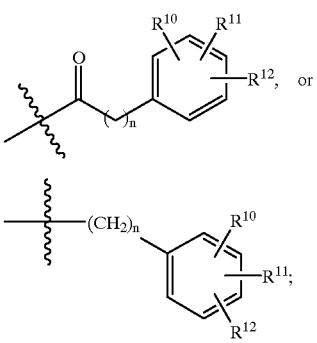

$R^3$, $R^4$, $R^5$, and $R^6$ are each, independently, hydrogen, or acyl of 2–7 carbon atoms;

$R^7$ is hydrogen, methyl, or phenyl;

$R^8$ is hydrogen, alkyl of 1–6 carbon atoms, alkoxy of 1–6 carbon atoms, phenyl, —CN, —NO$_2$, halogen, or —CF$_3$;

$R^9$ is hydrogen, —NO$_2$, halogen, alkyl of 1–6 carbon atoms, perfluoroalkyl of 1–6 carbon atoms, —NHCO$_2$R$^{13}$, —NR$^{14}$R$^{15}$,

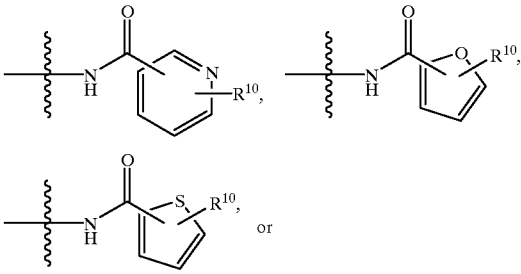

-continued

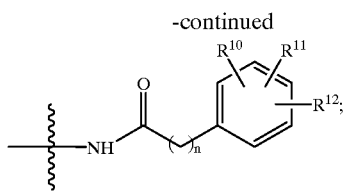

$R^{10}$, $R^{11}$, and $R^{12}$, are each, independently, hydrogen, alkyl of 1–6 carbon atoms, alkoxy of 1–6 carbon atoms, phenyl, —CN, —NO$_2$, halogen, —CF$_3$, acyl of 2–7 carbon atoms, or benzoyl, wherein the phenyl moiety of the benzoyl group is optionally mono-, di-, or tri-substituted with alkyl of 1–6 carbon atoms, alkoxy of 1–6 carbon atoms, —CN, —NO$_2$, halogen, or —CF$_3$;

$R^{13}$ is alkyl of 1–6 carbon atoms;

$R^{14}$ and $R^{15}$ are each, independently, hydrogen, acyl of 2–7 carbon atoms, perfluoroacyl of 2–7 carbon atoms; n=0–3;

or a pharmaceutically acceptable salt thereof.

Specifically preferred compounds of this invention are:

N-{5-[(2,3,2',3'-Tetra-O-acetyl-6-deoxy-6-benzylsulfanyl-4',6'-O-benzylidene-β-D-maltosyl)-oxy-methyl]-2-chloro-phenyl}-acetamide or a pharmaceutically acceptable salt thereof;

N-{5-[(4',6'-O-Benzylidene-6-deoxy-6-benzylsulfanyl-βD-maltosyl)-oxy-methyl]-2-chloro-phenyl}-acetamide or a pharmaceutically acceptable salt thereof;

N-(5-{[2,3,2',3'-Tetra-O-acetyl-6-deoxy-6-(2,4-dichloro-benzylsulfanyl)-4',6'-O-benzylidene-βD-maltosyl]-oxy-methyl}-2-chloro-phenyl)-acetamide or a pharmaceutically acceptable salt thereof;

N-(5-{[4',6'-O-Benzylidene-6-deoxy-6-(2,4-dichloro-benzylsulfanyl)-β-D-maltosyl]-oxy-methyl}-2-chloro-phenyl)-acetamide or a pharmaceutically acceptable salt thereof;

N-{5-[(2,3,2',3'-Tetra-O-acetyl-4',6'-O-benzylidene-6-deoxy-6-benzylsulfinyl-β-D-maltosyl)-oxy-methyl]-2-chloro-phenyl}-acetamide or a pharmaceutically acceptable salt thereof;

N-{5-[(4',6'-O-Benzylidene-6-deoxy-6-benzylsulfinyl-β-D-maltosyl)-oxy-methyl]-2-chloro-phenyl}-acetamide or a pharmaceutically acceptable salt thereof;

N-{5-[(4',6'-O-Benzylidene-6-deoxy-6-benzylsulfonyl-β-D-maltosyl)-oxy-methyl]-2-chloro-phenyl}-acetamide or a pharmaceutically acceptable salt thereof;

N-{5-[(2,2',3,3'-Tetra-O-acetyl-4',6'-O-benzylidene-6-deoxy-6-phenylsulfanyl-β-D-maltosyl)-oxy-methyl]-2-chloro-phenyl}-acetamide or a pharmaceutically acceptable salt thereof;

N-{5-[(4',6'-O-Benzylidene-6-deoxy-6-phenylsulfanyl-β-D-maltosyl)-oxy-methyl]-2-chloro-phenyl}-acetamide or a pharmaceutically acceptable salt thereof;

N-{5-[(2,2',3,3'-Tetra-O-acetyl-4',6'-O-benzylidene-6-deoxy-6-phenylsulfinyl-β-D-maltosyl)-oxy-methyl]-2-chloro-phenyl}-acetamide or a pharmaceutically acceptable salt thereof;

N-{5-[(4',6'-O-Benzylidene-6-deoxy-6-phenethylsulfanyl-β-D-maltosyl)-oxy-methyl]-2-chloro-phenyl}acetamide or a pharmaceutically acceptable salt thereof;

N-{5-[(2,2',3,3'-Tetra-O-acetyl-4',6'-O-benzylidene-6-deoxy-6-phenethylsulfanyl-β-D-maltosyl)-oxy-methyl]-2-chloro-phenyl}-acetamide or a pharmaceutically acceptable salt thereof;

N-(5-{[4',6'-O-Benzylidene-6-deoxy-6-(phenyl-ethyl-sulfinyl)-β-D-maltosyl]-oxy-methyl}-2-chloro-phenyl)-acetamide or a pharmaceutically acceptable salt thereof;

N-(5-{[4',6'-O-Benzylidene-6-deoxy-6-(3-phenyl-propylsulfanyl)-β-D-maltosyl]-oxy-methyl}-2-chloro-phenyl)-acetamide or a pharmaceutically acceptable salt thereof;

N-{5-[(4',6'-O-Benzylidene-6-deoxy-6-benzoylamino-β-D-maltosyl)-oxy-methyl]-2-chloro-phenyl}-acetamide or a pharmaceutically acceptable salt thereof;

N-(5-{[4',6'-O-Benzylidene-6-deoxy-6-(2-phenyl-1-oxo-ethyl-amino)-β-D-maltosyl]-oxy-methyl}-2-chloro-phenyl)-acetamide or a pharmaceutically acceptable salt thereof;

N-{5-[(4',6'-O-Benzylidene-6-deoxy-6-phenethylsulfanyl-β-D-maltosyl)-oxy-methyl]-2-chloro-phenyl}-carbamic acid methyl ester or a pharmaceutically acceptable salt thereof; and N-{5-[(4',6'-O-Benzylidene-6-deoxy-6-benzylsulfinyl-β-D-maltosyl)-oxy-methyl]-2-chloro-phenyl}-carbamic acid methyl ester or a pharmaceutically acceptable salt thereof.

The compounds of this invention were be prepared according to the following schemes from commercially available starting materials or starting materials which can be prepared using literature procedures. This scheme shows the preparation of representative compounds of this invention.

Acetobromomaltose 1 is coupled with a benzyl alcohol 2 in the presence of a catalyst such as a mercuric bromide, mercuric cyanide, silver triflate, or silver perchlorate in an aprotic solvent such as acetonitrile, dichloromethane, ether, toluene or nitromethane at temperatures ranging from −40° C. to reflux to yield glycoside 3 (Scheme 1). This glycosidation can also be accomplished using Schmidt's trichloroacetimidate coupling with zinc bromide in a solvent such as dichloromethane. Reduction of the nitro group of 3 can be accomplished with a reducing agent such as stannous chloride in a polar aprotic solvent such as ethyl acetate at ambient temperature to reflux to afford the anilino compound 4. Coupling of 4 with an acid chloride or a sulfonyl chloride can be completed in the presence of an amine base such as triethylamine or diisopropylethylamine or using a stronger base such as sodium hydride (for sterically hindered systems) in an aprotic solvent such as dichloromethane or tetrahydrofuran at temperatures ranging from 0° C. to ambient temperature to yield the target compound 5. The peracetylated compound 5 can be converted to the heptahydroxy compound 6 with catalytic sodium methoxide in methanol or aqueous sodium hydroxide in methanol at temperatures ranging from ambient temperature to reflux.

As illustrated in Scheme 2, the 4' and 6' groups of 6 can be reacted with an acetal in the presence of an acid catalyst such as camphorsulfonic acid or p-toluene sulfonic acid in a polar aprotic solvent such as N,N-dimethylformamide at temperatures ranging from 25° C. to reflux to give the acetal derivative 7.

Acetal 7 can be converted to the 6-tosylate 10 using tosyl chloride and pyridine in a solvent such as dichloromethane (Scheme 3); the resulting intermediate is then peracylated with an acid chloride or an acid anhydride in the presence of an amine base such as triethylamine or diisopropylethylamine in an aprotic solvent such as dichloromethane or tetrahydrofuran at temperatures ranging from 0° C. to ambient temperature to generate compound 11.

In Scheme 4, the tosylate intermediate 11 can be converted to a thioether via direct displacement with a sulfide nucleophile generated from a base such as sodium hydride and an appropriate thiol in a polar solvent such as N,N-dimethylformamide. This thioether intermediate can then be subjected to hydrolysis conditions as previously mentioned to afford 13 (W=S). Alternatively the thioether intermediate can be oxidized with one or two equivalents of m-chloroperoxybenzoic acid followed by hydrolysis to generate 13 as a sulfoxide or a sulfone respectively (W=SO or SO$_2$).

The C-6 position can also be converted to an amine or amide linkage by first converting the tosylate 11 to an azide (Scheme 5); this reaction can be accomplished using sodium azide in a polar solvent such as N,N-dimethylformamide at 50° C. The intermediate can be reduced to a primary amine with triphenylphosphine and 5% water in tetrahydrofuran. The amine can be coupled to an appropriate acid chloride in the presence of a base such as pyridine in an aprotic solvent such as tetrahydrofuran or dichloromethane followed by the standard hydrolysis conditions to afford compound 14. The intermediate amine or amide 14 can be alkylated with an alkyl halide in the presence of a base such as sodium hydride (for sterically hindered systems) in a polar solvent such as N,N-dimethylformamide at temperatures ranging from 0° C. to reflux.

If desired during the course of the synthetic sequence, the free hydroxyl groups of compounds 10, 13 and 14 can be derivatized. For example the free hydroxyl groups of compounds 10, 13 and 14 can be acylated with an acid chloride or an acid anhydride in the presence of an amine base such as triethylamine or diisopropylethylamine in an aprotic solvent such as dichloromethane or tetrahydrofuran at temperatures ranging from 0° C. to ambient temperature. Alternatively the free hydroxyl groups of compounds 10, 13 and 14 can be alkylated with an appropriate alkyl halide in the presence of a base such as sodium hydride or potassium hydroxide in a polar solvent such as N,N-dimethylformamide or DMSO at temperatures ranging from 0° C. to reflux.

Scheme 1

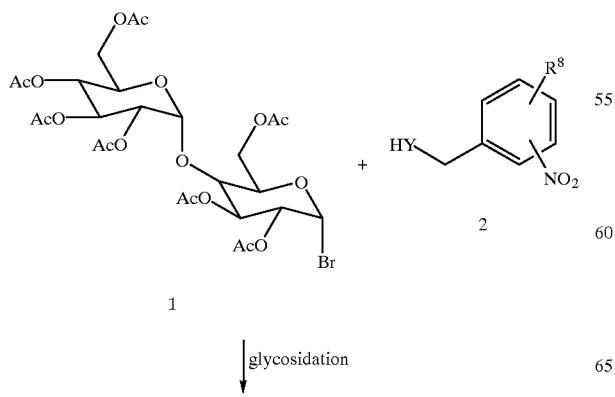

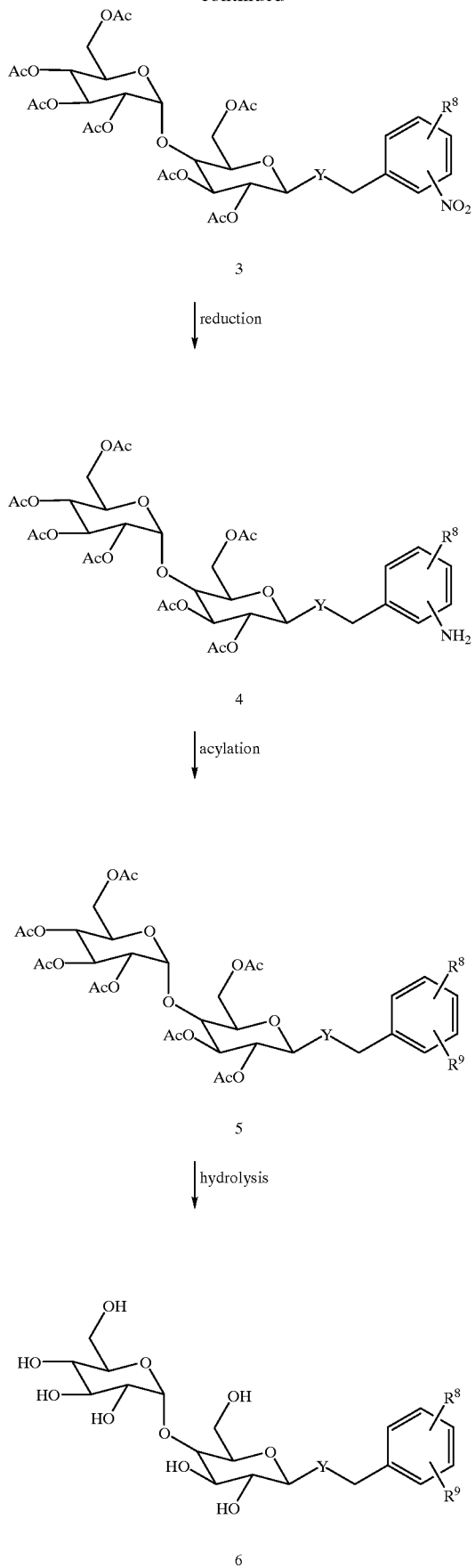

Scheme 2
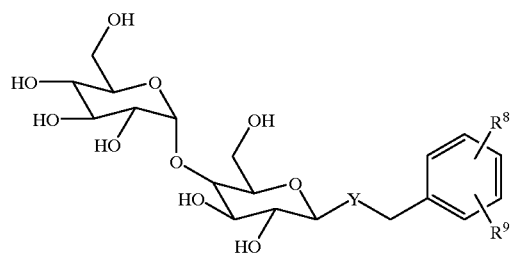
6
↓ C-4',6'-acetal formation
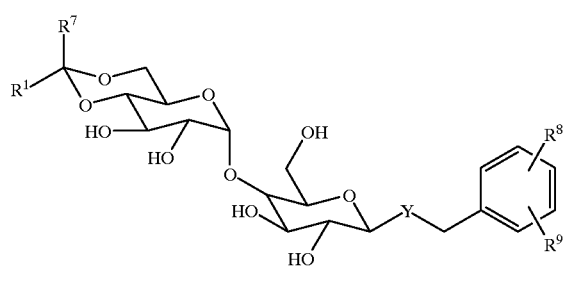
7
Scheme 3
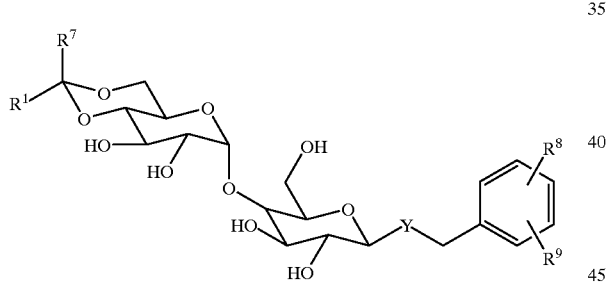
7
↓ tosylation
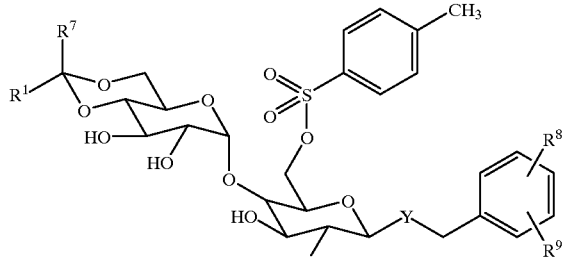
10
↓ peracetylation
-continued
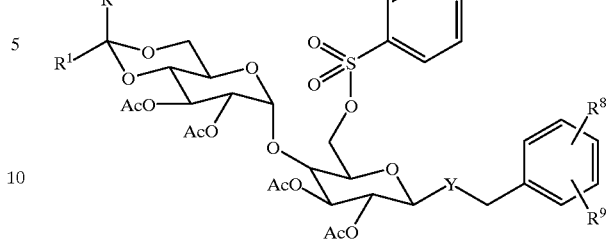
11
Scheme 4
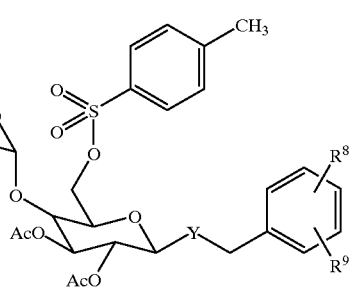
11
1) thioether formation
2) oxidation (for SO and SO$_2$)
3) hydrolysis
↓
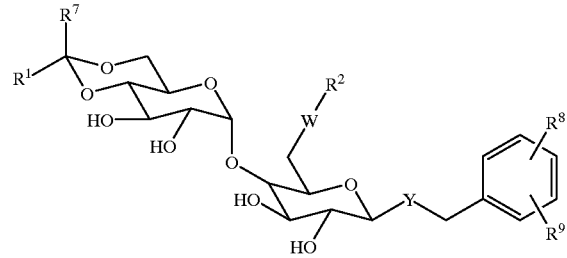
13
W = S, SO, or SO$_2$ Scheme 5

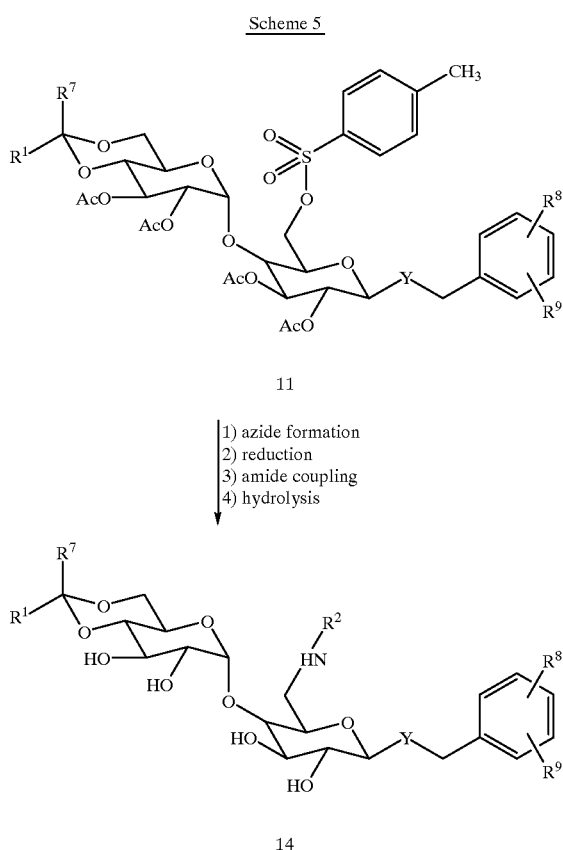

The compounds of this invention are useful as antiproliferative agents. The following procedures show the evaluation of representative compounds of this invention in standard pharmacological test procedure which measured ability of the evaluated compound to inhibit smooth muscle cell proliferation Effects of Compounds on Cell Proliferation Using $^3$H Thymidine Incorporation Human and porcine smooth muscle cells were tested in early passage (generally passage 3–7) at sub-confluent conditions. Cultures were grown in 16 mm (24 well) multi-well culture dishes in medium 199 supplemented with 10% fetal bovine serum and 2% antibiotic/antimycotic. At sub-confluence, the cells were placed in a defined serum free medium (AIM-V; Gibco) for 24–48 h prior to initiating the experimental protocol.

Although compounds were found to be more effective with longer pre-incubations, in general, the procedures were initiated with the addition of compound, $^3$H thymidine and serum/growth factor to serum deprived synchronized cells and results are reported accordingly.

Compounds were added to each well at 50 fold dilution (20 μL/well) and the plates were incubated for 24–36 h at 37° C. in 5% $CO_2$. Compounds were initially dissolved in 50% ethanol and serially diluted into media. Compounds were routinely evaluated at concentrations from 1 to 100 μM. As a control, grade II porcine intestinal mucosal heparin (sodium salt) was routinely evaluated in all cell preparations at concentrations from 0.1 to 100 μg/mL.

At the completion of the test procedure, plates were placed on ice, washed three times with ice cold phosphate buffered saline (PBS) and incubated in ice cold 10% trichloroacetic acid (TCA) got 30 min to remove acid soluble proteins. Solution was transferred to scintillation vials containing 0.4 N HCl (500 μL/vial to neutralize NaOH) and each well was rinsed two times with water (500 μL) for a total volume of 2 mL/vial.

Data was obtained, in triplicate, for both control and experimental samples. Control (100%) data was obtained from maximally stimulated cells, as the result of growth factor or serum stimulation. Experimental data was obtained from cells maximally stimulated with growth factor or serum and treated with compound. Data are expressed as an $IC_{50}$ in Table I below.

TABLE 1

| Compound of Example | Porcine Smooth Muscle Cell Antiproliferation $IC_{50}$ |
|---|---|
| 1 | 0.039 μM |
| 2 | 0.017 μM |
| 3 | 0.050 μM |
| 4 | 0.030 μM |
| 5 | 0.518 μM |
| 6 | 0.025 μM |
| 7 | 0.049 μM |
| 8 | 0.021 μM |
| 9 | 0.077 μM |
| 10 | 0.130 μM |
| 11 | 0.040 μM |
| 12 | 0.030 μM |
| 13 | 0.091 μM |
| 14 | 0.005 μM |
| 15 | 0.047 μM |
| 16 | 40% inhibition @50 μM |
| 17 | 0.032 μM |
| 18 | 0.170 μM |
| 19 | 0.169 μM |
| 20 | 0.035 μM |

The compounds of this invention are useful in treating or inhibiting diseases which are characterized by excessive smooth muscle cell proliferation (smooth muscle cell hyperproliferation). The compounds are particularly useful in treating hyperproliferative vascular diseases which are characterized by smooth muscle cell hyperproliferation, such as restenosis, which most frequently arises from vascular reconstuctive surgery and transplantation, for example, balloon angioplasty, vascular graft surgery, coronary atery bypass surgery, and heart transplantation. Other disease states in which there is unwanted "cellular" vascular proliferation include hypertension, astmha, and congestitive heart failure. The compounds of this invention are also usefull as inhibitors of angiogenesis. Angiogenesis (neovascularization), the process by which new capillaries are formed, is of principal importance for a number of pathological events including chronic inflammation and malignant processes. The compounds of this invention are therefore useful as antineoplastic agents.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.1 to 10 mg/kg administered parenterally (intravenous preferred), with projected daily oral dosage being approximately ten-fold higher. Anticipated intravenous administration would last for approximately 5–30 days following acute vascular injury (i.e., balloon angioplasty or transplantation) and for a longer duration for the treatment of chronic disorders. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packaged powders, vials, ampoules, pre filled syringes or sachets containing liquids. The unit dosage form can be, for example, a capsule or tablet itself, or it can be the appropriate number of any such compositions in package form.

The following provides the preparation of representative compounds of this invention.

EXAMPLE 1

N-{5-[(2,3,2',3'-Tetra-O-acetyl-6-deoxy-6-benzylsulfanyl-4',6'-O-benzylidene-β-D-maltosyl)-oxy-methyl]-2-chloro-phenyl}-acetamide Step 1

4-Chloro-3-nitro-benzyl-β-D-maltoside heptaacetate

To a stirred solution of 4-chloro-3-nitrobenzyl alcohol (6.70 g, 35.7 mmol) and $HgBr_2$ (14.2 g, 39.3 mmol) in freshly distilled $CH_3CN$ (239 mL) was added in one portion $Hg(CN)_2$ (9.02 g, 35.7 mmol). After 0.5 h, acetobromomaltose (25.0 g, 35.7 mmol) was added, and the mixture stirred for 18 h at rt. The reaction was then quenched with a mixture of $H_2O$:brine (1:1, 100 mL) and extracted with 10% $CH_2Cl_2$:EtOAc. The combined organic extracts were dried ($MgSO_4$) and concentrated. Purification on silica gel (10:90 to 80:20 EtOAc:petroleum ether gradient) gave 51.9 g (90%) of the title compound as a glassy oil which was recrystallized from $Et_2O$:petroleum ether to afford a glassy white solid, mp 107–111° C.; $^1H$ NMR ($CDCl_3$) δ 2.00 (s, 3H), 2.02 (s, 3H), 2.03, (s, 3H), 2.04 (s, 6H), 2.11 (s, 3H), 2.15 (s,3H), 3.70 (ddd, J=2.9, 4.2, 9.7 Hz, 1H), 3.94–3.98 (m, 1H), 4.01–4.07 (m, 2H), 4.20–4.28 (m, 2H), 4.54 (dd, J=2.9, 12.3 Hz, 1H), 4.63–4.68 (m, 2H), 4.84–4.94 (m, 3H), 5.06 (t, J=10.1 Hz, 1H), 5.26 (t, J=9.2 Hz, 1H), 5.36 (dd, J=9.7, 10.3 Hz, 1H), 5.42 (d, J=4.2 Hz, 1H), 7.43 (dd, J=2.2, 8.3 Hz, 1H), 7.53 (d, J=8.3 Hz, 1H), 7.83 (d, J=2.0 Hz, 1H); IR (KBr) 3450, 2950, 1755, 1550, 1375, 1230 and 1050 $cm^{-1}$; mass spectrum [(+) ESI], m/z 823/825 ($M+NH_4^+$), 828/830 $(M+Na)^+$; Anal. Calcd. for $C_{33}H_{40}ClNO_{20}$: C, 49.17; H, 5.00; N, 1.74, Found: C, 49.16; H, 4.88; N, 1.71.

Step 2

2-Chloro-5-(hepta-O-acetyl-β-D-maltosyl-oxymethyl)-phenylamine

A solution containing 4-chloro-3-nitro-benzyl-β-D-maltoside heptaacetate (19.3 g, 23.9 mmol) and tin (II) chloride dihydrate (37.7 g, 167 mmol) in EtOAc (479 mL) was refluxed for 2 h. The reaction was cooled to rt, carefully quenched with sat. aq. $NaHCO_3$ (until basic), diluted with EtOAc (250 mL), stirred for 0.5 h and filtered. The biphasic filtrate was separated and the aqueous phase extracted with EtOAc. The combined organic extracts were dried ($Na_2SO_4$) and concentrated. Purification on silica gel (0 to 12% acetone/$CHCl_3$ gradient) gave 17.8 g (96%) 2-Chloro-5-

(hepta-O-acetyl-β-D-maltosyl-oxymethyl)-phenylamine as a glassy solid, mp 78–79° C.; $^1$H NMR (CDCl$_3$) δ 2.00 (s, 9H), 2.026 (s, 3H), 2.032 (s, 3H), 2.11 (s, 3H), 2.16 (s 3H), 3.00–5.00 (bs, 2H), 3.64–3.68 (m, 1H), 3.97 (ddd, J=2.4, 4.2, 10.1 Hz, 1H), 4.02–4.07 (m, 2H), 4.24 (dd, J=2.2, 3.7, 1H), 4.27 (dd, J=2.6, 4.0 Hz, 1H), 4.50–4.57 (m, 3H), 4.74 (d, J=12.1 Hz, 1H), 4.83–4.90 (m, 2H), 5.05 (t, J=10.1 Hz, 1H), 5.22 (t, J=9.2 Hz, 1H), 5.35 (dd, J=9.7, 10.5 Hz, 1H), 5.42 (d, J=4.0 Hz, 1H), 6.62 (dd, J=2.0, 8.1 Hz, 1H), 6.76 (d, J=2.0 Hz, 1H), 7.21 (d, J=8.1 Hz, 1H); IR (KBr) 3450, 3350, 2950, 1755, 1650, 1425, 1375, 1230 and 1050 cm$^{-1}$; mass spectrum [(+) ESI], m/z 776/778 (M+H)$^+$, 798/800 (M+Na)$^+$; Anal. Calcd. for C$_{33}$H$_{42}$ClNO$_{18}$: C, 51.07; H, 5.45; N, 1.80, Found: C, 50.94; H, 5.52; N, 1.60.

Step 3

N-[2-Chloro-5-(hepta-O-acetyl-β-D-maltosyl-oxymethyl)-phenyl]-acetamide

To a stirred solution of 2-chloro-5-(hepta-O-acetyl-β-D-maltosyl-oxymethyl)-phenylamine (20.6 g, 26.5 mmol) and triethylamine (8.13 mL, 58.3 mmol) in THF (265 mL) at 0° C. was added dropwise acetyl chloride (2.26 mL, 31.8 mmol). After 0.5 h at this temperature, it was warmed to rt and stirred an additional 6 h. At this point, the reaction was concentrated and taken up in EtOAc (700 mL). This organic solution was washed with 1 N HCl (70 mL), sat. aq. NaHCO$_3$ (70 mL), and brine (70 mL) and then dried (MgSO$_4$). After concentration, the residue was purified on silica gel (20:80 to 100:0 EtOAc:petroleum ether gradient) to afford the product (16.2 g, 75%) as a glassy solid, mp 84–86° C.; $^1$H NMR (CDCl$_3$) δ 2.00 (s, 6H), 2.020 (s, 3H), 2.027 (s, 3H), 2.03 (s, 3H), 2.11 (s, 3H), 2.16 (s, 3H), 2.24 (s, 3H), 3.66–3.69 (m, 1H), 3.94–3.98 (m, 1H), 4.00–4.06 (m, 2H), 4.22–4.28 (m, 2H), 4.50–4.61 (m, 3H), 4.80–4.91 (m, 3H), 5.05 (t, J=10.1 Hz, 1H), 5.22 (t, J=9.2 Hz, 1H), 5.35 (dd, J=9.4, 10.5 Hz, 1H), 5.41 (d, J=4.0 Hz, 1H), 6.99 (dd, J=2.0, 8.1 Hz, 1H), 7.34 (d, J=8.1 Hz, 1H), 7.62 (s, 1H), 8.32 (s, 1H); IR (KBr) 3400, 2950, 1750, 1690, 1600, 1540, 1425, 1375, 1230 and 1050 cm$^{-1}$; mass spectrum [(+) ESI], m/z 818/820 (M+H)$^+$, 840 (M+Na)$^+$; Anal. Calcd. for C$_{35}$H$_{44}$ClNO$_{19}$: C, 51.38; H, 5.42; N, 1.71, Found: C, 51.03; H, 5.36; N, 1.59.

Step 4

N-[2-Chloro-5-(β-D-maltosyl-oxymethyl)-phenyl]-acetamide

A solution containing N-[2-chloro-5-(hepta-O-acetyl-β-D-maltosyl-oxymethyl)-phenyl]-acetamide (0.945 g, 1.12 mmol) and 25 weight % NaOMe in MeOH (19.2 μL, 0.336 mmol) in MeOH (27.6 ml) was refluxed for 2.5 h. The reaction was cooled to room temperature and concentrated, and the resulting residue was triturated with Et$_2$O to afford the product (0.583 g, 99%) as a foam; $^1$H NMR (DMSO-d$_6$) δ 2.07 (s, 3H), 3.03–3.16 (m 2H), 3.19–3.49 (m, 7H), 3.55–3.62 (m, 2H), 3.67–3.73 (m, 1H), 4.28 (d, J=7.7 Hz, 1H), 4.33–5.76 (bs, 7H), 4.67 (ABq, J=12.5 Hz, Δδ=0.22, 2H), 5.01 (d, J=3.7 Hz, 1H), 7.21 (dd, J=1.8, 8.1 Hz, 1H), 7.44 (d, J=8.1 Hz, 1H), 7.64 (d, J=1.5 Hz, 1H), 9.33–9.69 (bs, 1H); IR (KBr) 3400, 2900, 1680, 1600, 1540, 1430, 1375, 1310, 1150 and 1035 cm$^{-1}$, mass spectrum [(+) ESI], m/z 524/526 (M+H)$^+$, 546 (M+Na)$^+$; Anal. Calcd. for C$_{21}$H$_{30}$ClNO$_{12}$·1.0 MeOH: C, 47.53; H, 6.16; N, 2.52. Found: C, 47.94; H, 6.34; N, 2.42.

Step 5

N-{5-[(4',6'-O-Benzylidene-β-D-maltosyloxy)-methyl]-2-chloro-phenyl}-acetamide

To a stirred solution of N-[2-chloro-5-(β-D-maltosyl-oxymethyl)-phenyl]-acetamide (14.15 g, 27.0 mmol) in DMF (325 mL) at rt was added benzaldehyde dimethyl acetal (8.11 mL, 54.0 mmol) dropwise followed by TsOH·H$_2$O (2.57 g, 13.5 mmol). The reaction mixture was heated to 60° C. for 6 h and then quenched with K$_2$CO$_3$ (1.87 g, 13.5 mmol) with an additional 0.5 h heating at this temperature. At this point, the solution was filtered hot, and the solvent was distilled off using the high vac. The residue was purified on silica gel (80:2:1 to 20:2:1 EtOAc:EtOH:H$_2$O gradient) to afford the product (10.8 g, 65%) as a white solid, mp 143–147° C.; $^1$H NMR (DMSO-d$_6$) δ 2.08 (s, 3H), 3.07–3.12 (m, 1H), 3.28–3.50 (m, 5H), 3.51–3.60 (m, 2H), 3.64–3.75 (m, 3H), 4.10–4.12 (m, 1H), 4.30 (d, J=7.9 Hz, 1H), 4.67 (t, 5.9 Hz, 1H), 4.68 (ABq, J=12.5 Hz, Δδ=0.22, 2H), 5.14 (d, J=4.0 Hz, 1H), 5.25 (d, J=5.1 Hz, 1H), 5.30 (d, J=5.3 Hz, 1H), 5.51 (d, J=3.3 Hz, 1H), 5.57 (s, 1H), 5.63 (d, J=6.8 Hz, 1H), 7.22 (dd, J=1.5, 8.3 Hz, 1H), 7.35–7.38 (m, 3H), 7.42–7.46 (m, 3H), 7.66 (s, 1H), 9.53 (s, 1H); IR (KBr) 3500, 3410, 2910, 2850, 1700, 1600, 1550, 1440, 1425, 1375, 1310, 1230, 1150, 1070, and 1030 cm$^{-1}$; mass spectrum [(+) FAB], m/z 634 (M+Na)$^+$; Anal. Calcd. for C$_{28}$H$_{34}$ClNO$_{12}$·1.0 H$_2$O: C, 53.38; H, 5.76; N, 2.22, Found: C, 53.58; H, 5.62; N, 2.25.

Step 6

N-(5-{[4',6'-O-Benzylidene-6-O-(4-toluenesulfonyl)-β-D-maltosyl]-oxy-methyl}-2-chloro-phenyl)-acetamide At 0° C., to a stirred solution of N-{5-[(4',6'-O-benzylidene-β-D-maltosyloxy)-methyl]-2-chloro-phenyl}-acetamide (1.81 g, 2.96 mmol) in pyridine (6.0 mL) was added a solution of p-toluenesulfonyl chloride (0.686 g, 3.60 mmol) in CH$_2$Cl$_2$ (3.75 mL). After 2 h, additional p-toluenesulfonyl chloride (0.686 g, 3.60 mmol) in CH$_2$Cl$_2$ (3.75 mL) was added and the solution was stirred at 0° C. for 2 h. The reaction was quenched with ice cold H$_2$O (50 mL) and extracted with EtOAc. The combined organic extracts were washed successively with sat. aq. NaHCO$_3$ (2×), sat. aq. CuSO$_4$ (2×), brine (2×), dried (Na$_2$SO$_4$) and concentrated. Purification on silica gel (5–10% MeOH:CH$_2$Cl$_2$ gradient) gave 0.930 g, (41%) of a white solid, mp 105–120° C.; $^1$H NMR (DMSO-d$_6$) δ 2.08 (s, 3H), 2.33 (s, 3H), 3.04–3.09 (m, 1H), 3.27–3.45 (m, 4H), 3.49–3.53 (m, 1H), 3.60–3.65 (m, 3H), 3.95 (d, 1H), 4.13 (dd, 1H), 4.29–4.33 (m, 2H), 4.46 (d, 1 H), 4.62 (d, 1 H), 5.05 (d, 1H), 5.33–5.35 (m, 2H), 5.55 (d, 1H), 5.57 (s, 1H), 5.75 (d, 1H), 7.18 (d, 1H), 7.35–7.47 (m, 8H), 7.78 (d, 2H), 9.53 (s, 1H); mass spectrum [(+) ESI], m/z 766/768 (M+H)$^+$, 783/785 (M+NH$_4$)$^+$; Anal. Calcd. for C$_{35}$H$_{40}$NClO$_{14}$S·H$_2$O: C, 53.60; H, 5.40; N, 1.79, Found: C, 53.46; H, 5.18; N, 1.80.

Step 7

N-(5-{[2,3,2',3'-Tetra-O-acetyl-4',6'-O-benzylidene-6-O-(4-toluenesulfonyl)-β-D-maltosyl]-oxy-methyl}-2-chloro-phenyl)-acetamide At 0° C., to a stirred solution containing N-(5-{[4',6'-O-benzylidene-6-O-(4-toluenesulfonyl)-β-D-maltosyl]-oxy-methyl}-2-chloro-phenyl)-acetamide (0.782 g, 1.02 mmol), pyridine (0.991 mL, 12.3 mmol) and 4-dimethylaminopyridine (0.457 g, 4.08 mmol) in CH$_2$Cl$_2$ (20 mL) was added acetic anhydride (0.764 mL, 8.17 mmol). After 2 h, the reaction was diluted with diethyl ether (100 mL), washed successively with H$_2$O (2×), with sat. aq. NaHCO$_3$ (2×), with sat. aq. CuSO$_4$ (2×), with brine (2×), dried (Na$_2$SO$_4$) and concentrated. Purification on silica gel (1,2 and 3% MeOH/CHCl$_3$ gradient) gave 0.942 g (99%) of title compound as a white solid, mp 116–122° C.; $^1$H NMR (DMSO-d$_6$) δ 1.91 (s, 3H), 1.92 (s, 3H), 1.96 (s, 3H), 2.00 (s, 3H), 2.08 (s, 3H), 2.29 (s, 3H), 3.68 (dd, 1H), 3.77 (t, 1H), 3.85 (t, 1H), 3.90 (t, 1H), 3.97–4.00 (m, 1H), 4.21 (dd, 1H), 4.32 (s, 2H), 4.39 (d, 1H), 4.56 (d, 1H), 4.60 (d, 1H), 4.78 (d, 1H), 4.86 (dd, 1H), 5.17–5.30 (m, 3H), 5.65 (s, 1H), 7.03

(d, 1H), 7.34–7.41 (m, 7H), 7.46 (d, 1H), 7.59 (s, 1H), 7.80 (d, 2H), 9.52 (s, 1H); mass spectrum [(+) ESI], m/z 934/936 (M+H)$^+$; Anal. Calcd. for $C_{43}H_{48}NClO_{18}S$: C, 55.27; H, 5.17; N, 1.50, Found: C, 55.07; H, 5.05; N, 1.47.

Step 8

N-{5-[(2,3,2',3'-Tetra-O-acetyl-6-deoxy-6-benzylsulfanyl-4',6'-O-benzylidene-β-D-maltosyl)-oxy-methyl]-2-chloro-phenyl}-acetamide At ambient temperature, to a solution of benzyl mercaptan (43.3 μl, 0.370 mmol) in DMF (1 mL) was added 60% sodium hydride/mineral oil (13.4 mg, 0.336 mmol) and the mixture was stirred for 0.5 h. To the reaction was added a solution of N-(5-{[2,3,2',3'-tetra-O-acetyl-4',6'-O-benzylidene-6-O-(4-toluenesulfonyl)-β-D-maltosyl]-oxy-methyl}-2-chloro-phenyl)-acetamide (0.314 g, 0.336 mmol) in DMF (2 mL). After 1 h, the reaction was quenched with ice cold H$_2$O (50 mL) and extracted with EtOAc. The organic extracts were dried (Na$_2$SO$_4$) and concentrated. Purification on silica gel eluting with 40% acetone/hexane followed by crystallization from EtOAc:hexane gave 0.236 g (79%) of the title compound as a white solid, mp 185° C.; $^1$H NMR (DMSO-d$_6$) δ 1.91 (s, 3H), 1.94 (s, 3H), 1.96 (s, 3H), 2.00 (s, 3H), 2.07 (s, 3H), 2.76 (dd, 1H), 2.87 (d, 1H), 3.68–3.71 (m, 1H), 3.74–3.92 (m, 6H), 4.18 (dd, 1H), 4.58 (d, 1H), 4.68–4.83 (m, 3H), 4.87 (dd, 1H), 5.20–5.29 (m, 3H), 5.63 (s, 1H), 7.08 (dd, 1H), 7.14–7.19 (m, 1H), 7.26–7.32 (m, 4H), 7.34–7.40 (m, 5H), 7.45 (d, 1H), 7.65 (s, 1H), 9.50 (s, 1H); IR (KBr) 3400, 2900, 1750, 1380, 1240 and 1075 cm$^{-1}$; mass spectrum [(+) FAB], m/z 886/888 (M+H)$^+$, 908/910 (M+Na)$^+$; Anal. Calcd. for $C_{43}H_{48}NClO_{15}S$: C, 58.27; H, 5.46; N, 1.58, Found: C, 58.12; H, 5.39; N, 1.60.

EXAMPLE 2

N-{5-[(4',6'-O-Benzylidene-6-deoxy-6-benzylsulfanyl-β-D-maltosyl)-oxy-methyl]-2-chloro-phenyl}-acetamide A solution containing N-{5-[(2,3,2',3'-tetra-O-acetyl-6-deoxy-6-benzylsulfanyl-4',6'-O-benzylidene-β-D-maltosyl)-oxy-methyl]-2-chloro-phenyl}-acetamide (0.148 g, 0.167 mmol) and 25 weight % NaOMe in MeOH (18 mg, 0.0835 mmol) in MeOH (4 mL) was refluxed for 3 h. The reaction was cooled to room temperature and concentrated. Purification on silica gel eluting with 10% MeOH:CH$_2$Cl$_2$ followed by crystallization from CH$_2$Cl$_2$:petroleum ether gave 0.100 g (83%) of title compound as a white solid, mp 96–110° C.; $^1$H NMR (DMSO-d$_6$) δ 2.06 (s, 3H), 2.62 (dd, 1H), 2.86 (dd, 1H), 3.11 (dd, 1H), 3.35–3.55 (m, 6H), 3.64 (d, 2H), 3.79 (dd, 2H), 3.99 (d, 1H), 4.30 (d, 1H), 4.59 (d, 1H), 4.76 (d, 1H), 5.16 (d, 1H), 5.31 (d, 2H), 5.50 (d, 1H), 5.56 (s, 1H), 5.65 (d, 1H), 7.18–7.23 (m, 2H), 7.26–7.31 (m, 4H), 7.35–7.38 (m, 3H), 7.43–7.46 (m, 3H), 7.68 (s, 1H), 9.51 (s, 1H); mass spectrum [(+) FAB], m/z 718/720 (M+H)$^+$; Anal. Calcd. for $C_{35}H_{40}NClO_{11}S.0.5\ H_2O$: C, 57.81; H, 5.68; N, 1.93, Found: C, 57.78; H, 5.62; N, 1.94. Found: C, 57.65; H, 5.56; N, 1.94.

EXAMPLE 3

N-(5-{[2,3,2',3'-Tetra-O-acetyl-6-deoxy-6-(2,4-dichloro-benzylsulfanyl)-4',6'-O-benzylidene-β-D-maltosyl]-oxy-methyl}-2-chloro-phenyl)-acetamide The title compound was prepared as a white solid (0.222 g, 70%) from 2,4-dichlorobenzylmercaptan using a procedure similar to step 8 of Example 1, mp 190 ° C.; $^1$H NMR (DMSO-d$_6$) δ 1.91 (s, 3H), 1.94 (s, 3H), 1.96 (s, 3H), 2.00 (s, 3H), 2.06 (s, 3H), 2.84 (dd, 1H), 2.96 (d, 1H), 3.69–3.80 (m, 2H), 3.84–3.96 (m, 5H), 4.19 (dd, 1H), 4.57 (d, 1H), 4.68–4.76 (m, 2H), 4.83 (d, 1H), 4.87 (dd, 1H), 5.22 (d, 1H), 5.26–5.31 (m, 2H), 5.63 (s, 1H), 7.07 (dd, 1H), 7.31 (dd, 1H), 7.34–7.38 (m, 5H), 7.41–7.45 (m, 2H), 7.58 (d, 1H), 7.64 (s, 1H), 9.49 (s, 1H); IR (KBr) 3400, 2900, 1760, 1370, 1240 and 1050 cm$^{-1}$; mass spectrum [(+) FAB], m/z 954/956/958/960 (M+H)$^+$; Anal. Calcd. for $C_{43}H_{46}NCl_3O_{15}S$: C, 54.07; H, 4.85; N, 1.47, Found: C, 53.96; H, 4.73; N, 1.52.

EXAMPLE 4

N-(5-{[4',6'-O-Benzylidene-6-deoxy-6-(2,4-dichloro-benzylsulfanyl)-β-D-maltosyl]-oxy-methyl}-2-chloro-phenyl)-acetamide A solution containing N-(5-{[2,3,2',3'-tetra-O-acetyl-6-deoxy-6-(2,4-dichloro-benzylsulfanyl)-4',6'-O-benzylidene-β-D-maltosyl]-oxy-methyl}-2-chloro-phenyl)-acetamide and 25 weight % NaOMe in MeOH (16.1 mg, 0.0743 mmol) in MeOH (4 mL) was refluxed for 3 h. The reaction was slowly cooled to 0° C. The resulting crystals were collected and dried to give 63 mg, (99%) of title compound as a white solid, mp 125–128° C.; $^1$H NMR (DMSO-d$_6$) δ 2.06 (s, 3H), 2.71 (dd, 1H), 2.93 (dd, 1H), 3.12 (t, 1H), 3.37–3.40 (m, 2H), 3.43–3.46 (m, 2H), 3.54 (t, 2H), 3.65 (d, 2H), 3.87 (s, 2H), 4.00 (d, 1H), 4.32 (d, 1H), 4.58 (d, 1H), 4.75 (d, 1H), 5.16 (d, 1H), 5.35 (br. s, 2H), 5.55 (br. s, 2H), 5.56 (s, 1H), 7.20 (dd, 1H), 7.33–7.38 (m, 4H), 7.42–7.45 (m, 4H), 7.58 (d, 1H), 7.66 (s, 1H), 9.50 (s, 1H); mass spectrum [(+) FAB], m/z 786/788/790/792 (M+H)$^+$; Anal. Calcd. for $C_{35}H_{38}NCl_3O_{11}S.0.5\ H_2O$: C, 52.80; H, 4.94; N, 1.76, Found: C, 52.82; H, 4.77; N, 1.76. Found: C, 52.70; H, 4.77; N, 1.70.

EXAMPLE 5

N-{5-[(2,3,2',3'-Tetra-O-acetyl-4',6'-O-benzylidene-6-deoxy-6-benzylsulfinyl-β-D-maltosyl)-oxy-methyl]-2-chloro-phenyl}-acetamide At ambient temperature, to a stirred biphasic solution of N-{5-[(2,3,2',3'-Tetra-O-acetyl-6-deoxy-6-benzylsulfanyl-4',6'-O-benzylidene-β-D-maltosyl)-oxy-methyl]-2-chloro-phenyl}-acetamide (14.48 g, 16.34 mmol) in CH$_2$Cl$_2$ (163 mL) and sat. aq. NaHCO$_3$ (163 mL) was added in one portion 85% 3-chloroperoxybenzoic acid (3.32 g, 16.34 mmol). After 1 h, the reaction was quenched with brine (150 mL) and extracted with EtOAc. The combined organic extracts were dried (Na$_2$SO$_4$) and concentrated. Purification on silica gel eluting with a 1,2 and 3% MeOH:CHCl$_3$ gradient gave 12.89 g (87%) of title compound as a 1:1 mixture of diastereomers, white solid, mp 212–213° C.; $^1$H NMR (DMSO-d$_6$) δ 1.91, 1.92 (2s, 3H), 1.93, 1.95 (2s, 3H), 1.96, 1.97 (2s, 3H), 2.00, 2.01 (2s, 3H), 3.01–3.11 (m, 2H), 3.74–4.08 (m, 6H), 4.21–4.32 (m, 2H), 4.57 (t, J=13.0 Hz, 1H), 4.70–4.93 (m, 4H), 5.19–5.33 (m, 3H), 5.64, 5.68 (2s, 1H), 7.07 (d, 1H), 7.27–7.39 (m, 9H), 7.44 (dd, 2H), 7.62, 7.63 (2s, 1H), 9.51 (s, 1H); IR (KBr) 3400, 2920, 1750, 1375, 1240 and 1050 cm$^{-1}$; mass spectrum [(+) FAB], m/z 902/904 (M+H)$^+$; Anal. Calcd. for $C_{43}H_{48}NClO_{16}S$: C, 57.24; H, 5.36; N, 1.55, Found: C, 56.85; H, 5.19; N, 1.51.

EXAMPLES 6–8

N-{5-[(4',6'-O-Benzylidene-6-deoxy-6-benzylsulfinyl-β-D-maltosyl)-oxy-methyl]-2-chloro-phenyl}-acetamide Example 6 (racemate); Example 7 (diastereomer #1); Example 8 (diastereomer #2)

The title compound was prepared as a 1:1 mixture of diastereomers, white solid (0.068 g, 99%) from N-{5-[(2,3, 2',3'-tetra-O-acetyl-4',6'-O-benzylidene-6-deoxy-6-benzylsulfinyl-β-D-maltosyl)-oxy-methyl]-2-chloro-phenyl}-acetamide using a procedure similar to Example 2, mp 128–133° C.; $^1$H NMR (DMSO-d$_6$) δ 2.06 (s, 3H), 2.96–3.05 (m, 1H), 3.11–3.18 (m, 1H), 3.25–3.72 (m, 8H), 3.88–3.98 (m, 2H), 4.06–4.10 (m, 1H), 4.18, 4.22 (2d, 1H), 4.35, 4.44 (2d, 1H), 4.56, 4.60 (2d, 1H), 4.72, 4.76 (2d, 1H), 5.18, 5.20 (2d, 1H),5.34–5.39 (m, 2H), 5.56–5.59 (m, 2H), 5.67, 5.75 (2d, 1H), 7.19 (d, 1H), 7.29–7.37 (m, 9H), 7.41–7.47 (m, 2H), 7.65 (s, 1H), 9.51 (s, 1H); mass spectrum [(+) FAB], m/z 734/736 (M+H)$^+$; Anal. Calcd. for C$_{35}$H$_{40}$NClO$_{12}$S. 0.5 H$_2$O: C, 56.56; H, 5.56; N, 1.88, Found: C, 56.44; H, 5.38; N, 1.85.

The racemic mixture was separated by HPLC (Primesphere SIL; 5% MeOH:CH$_2$Cl$_2$) to give the two opposite sulfoxide diastereomers:

Diastereomer #1, a white solid, mp 214–215° C.; $^1$H NMR (DMSO-d$_6$) δ 2.06 (s, 3 H), 2.99 (dd, J=13.9, 7.6 Hz, 1H), 3.13–3.18 (m, 1H), 3.25–3.59 (m, 6H), 3.61–3.72 (m, 2H), 3.88–3.93 (m, 1H), 4.07 (dd, 1H), 4.08 (ABq, J=12.7 Hz, Δδ=0.10, 2H), 4.44 (d, J=7.7 Hz, 1H), 4.68 (ABq, J=12.5 Hz, Δδ=0.06, 2H), 5.18 (d, J=3.7 Hz, 1H), 5.34 (d, J=5.3 Hz, 1H), 5.38 (d, J=5.3 Hz, 1H), 5.56 (s, 1H), 5.58 (d, J=2.9 Hz, 1H), 5.75 (d, J=6.6 Hz, 1H), 7.19 (dd, J=8.2, 1.9 Hz, 1H), 7.28–7.37 (m, 8H), 7.41–7.45 (m, 3H), 7.65 (s, 1H), 9.51 (s, 1H); IR (KBr) 3400, 2900, 1675, 1070 and 700 cm$^{-1}$; mass spectrum [(−) FAB], m/z 732 (M−H)$^-$; Anal. Calcd. for C$_{35}$H$_{40}$NClO$_{12}$S.0.5 H$_2$O: C, 56.56; H, 5.56; N, 1.88, Found: C, 56.59; H, 5.51; N, 1.98.

Diastereomer #2, a white solid, mp 202–208° C.; $^1$H NMR (DMSO-d$_6$) δ 2.06 (s, 3H), 2.99–3.05 (m, 2H), 3.11–3.16 (m, 1H), 3.36–3.42 (m, 3H), 3.46–3.56 (m, 2H), 3.65–3.72 (m, 3H), 4.05 (ABq, J=13.0 Hz, Δδ=0.15, 2H), 4.09 (d, J=4.8 Hz, 1H), 4.35 (d, J=7.9 Hz, 1H), 4.65 (ABq, J=12.4 Hz, Δδ=0.07, 2H), 5.20 (d, J=4.0 Hz, 1H), 5.34 (d, 2H), 5.56 (d, J=3.1 Hz, 1H), 5.58 (s, 1H), 5.67 (d, J=6.6 Hz, 1H), 7.18 (dd, J=8.2, 1.9 Hz, 1H), 7.28–7.38 (m, 8H), 7.42–7.48 (m, 3H), 7.65 (s, 1H), 9.51 (s, 1H); IR (KBr) 3400, 2900, 1675, 1070 and 700 cm$^{-1}$; mass spectrum [(−) FAB], m/z 732 (M−H)$^-$; Anal. Calcd. for C$_{35}$H$_{40}$NClO$_{12}$S: C, 57.26; H, 5.49; N, 1.91, Found: C, 56.90; H, 5.64; N, 1.95.

EXAMPLE 9

N-{5-[(4',6'-O-Benzylidene-6-deoxy-6-benzylsulfonyl-β-D-maltosyl)-oxy-methyl]-2-chloro-phenyl}-acetamide Step 1

N-{5-[(2,2',3,3'-Tetra-O-acetyl-4',6'-O-benzylidene-6-deoxy-6-benzylsulfonyl-β-D-maltosyl)-oxy-methyl]-2-chloro-phenyl}-acetamide At ambient temperature, to a biphasic solution of N-{5-[(2,3,2',3'-tetra-O-acetyl-6-benzylsulfanyl-4',6'-O-benzylidene-β-D-maltosyl)-oxy-methyl]-2-chloro-phenyl}-acetamide (0.287 g, 0.324 mmol) in CH$_2$Cl$_2$ (5 mL) and sat. aq. NaHCO$_3$ (5 mL) was added in one portion 80% 3-chloroperoxybenzoic acid (0.147 g, 0.681 mmol). After 1 h, the reaction was quenched with brine (150 mL) and extracted with EtOAc. The combined organic extracts were dried (Na$_2$SO$_4$) and concentrated. Purification on silica gel (1,2 and 3% MeOH:CHCl$_3$ gradient) gave 0.244 g (82%) of N-{5-[(6-benzylsulfonyl-2,2',3,3'-tetra-O-acetyl-4',6'-O-benzylidene-β-D-maltosyl)-oxy-methyl]- 2-chloro-phenyl}-acetamide; $^1$H NMR (DMSO-d$_6$) δ 1.94 (s, 3H), 1.96 (s, 3H), 1.98 (s, 3H), 2.00 (s, 3H), 2.07 (s, 3H), 3.47–3.61 (m, 2H), 3.75–3.81 (m, 2H), 3.91 (t, J=9.2 Hz, 1H), 4.01 (t, J=9.2 Hz, 1H), 4.19 (d, J=5.6 Hz, 1H), 4.30–4.34 (m, 1H), 4.53 (s, 2H), 4.64 (d, J=12.6 Hz, 1H), 4.74–4.80 (m, 2H), 4.83–4.98 (m, 1H), 5.23–5.30 (m, 2H), 5.37 (t, J=9.2 Hz, 1H), 5.64 (s, 1H), 7.08 (dd, J=6.4, 1.8 Hz, 1H), 7.33–7.46 (m, 11H), 7.66 (s, 1H), 9.51 (s, 1H).

Step 2

N-{5-[(4',6'-O-Benzylidene-6-deoxy-6-benzylsulfonyl-β-D-maltosyl)-oxy-methyl]-2-chloro-phenyl}-acetamide The title compound was prepared as a white solid (0.118 g, 67%) from N-{5-[(2,2',3,3'-tetra-O-acetyl-4',6'-O-benzylidene-6-deoxy-6-benzylsulfonyl-β-D-maltosyl)-oxy-methyl]-2-chloro-phenyl}-acetamide using a procedure similar to Example 2, mp >225° C.; $^1$H NMR (DMSO-d$_6$) δ 2.05 (s, 3H), 3.15–3.20 (m, 1H), 3.36–3.46 (m, 4H), 3.49–3.59 (m, 3H), 3.60–3.69 (m, 2H), 3.94 (t, J=9.2 Hz, 1H), 4.00 (q, 1H), 4.40 (d, J=13.6 Hz, 1H), 4.50 (d, J=13.4, 1H), 4.52 (d, J=7.7 Hz, 1H), 4.66 (d, J=12.5 Hz, 1H), 4.81 (d, J=12.5 Hz, 1H), 5.12 (d, J=4.0 Hz, 1H), 5.37 (d, J=5.3 Hz, 1H), 5.41 (d, J=5.5 Hz, 1H), 5.55 (s, 2H), 5.78 (d, J=6.6, 1H), 7.19 (dd, J=8.3, 2.0 Hz, 1H), 7.33–7.44 (m, 11H), 7.67 (s, 1H), 9.48 (s, 1H); mass spectrum [(+) ESI], m/z 750/752 (m+H)$^+$; Anal. Calcd. for C$_{35}$H$_{40}$NClO$_{13}$S: C, 56.03; H, 5.37; N, 1.87, Found: C, 55.84; H, 5.23; N, 1.78.

EXAMPLE 10

N-{5-[(2,2',3,3'-Tetra-O-acetyl-4',6'-O-benzylidene-6-deoxy-6-phenylsulfanyl-β-D-maltosyl)-oxy-methyl]-2-chloro-phenyl}-acetamide At ambient temperature, to a solution of thiophenol (0.0257 mL, 0.250 mmol) in DMF (2.27 mL) was added 95% potassium-t-butoxide (26.8 mg, 0.227 mmol) and the mixture was stirred for 0.5 h. To the reaction was added in one portion N-(5-{[2,3,2',3'-tetra-O-acetyl-4',6'-O-benzylidene-6-O-(4-toluenesulfonyl)-β-D-maltosyl]-oxy-methyl}-2-chloro-phenyl)-acetamide (0.212 g, 0.227 mmol). After 16 h, the reaction was quenched with ice cold H$_2$O (50 mL) and extracted with EtOAc. The organic extracts were dried (Na$_2$SO$_4$) and concentrated. Purification on silica gel (40% acetone:hexane) followed by crystallization from EtOAc:hexane gave 98 mg (49%) of title compound as a white solid, mp 173–177° C.; $^1$H NMR (DMSO-d$_6$) δ 1.92 (s, 3H), 1.94 (s, 3H), 1.97 (s, 3H), 1.99 (s, 3H), 2.07 (s, 3H), 3.34–3.47 (m, 2H), 3.73–3.85 (m, 2H), 3.90 (d, J=9.4 Hz, 1H), 3.95 (d, J=9.0 Hz, 1H), 4.02–4.05 (m, 1H), 4.17 (dd, J=9.0, 5.3 Hz, 1H), 4.52 (ABq, J=12.5 Hz, Δδ=0.06, 2H), 4.70 (dd, J=9.6, 8.0 Hz, 1H), 4.84 (d, 1H), 4.89 (dd, J=10.2, 4.1 Hz, 1H), 5.24–5.32 (m, 3H), 5.61 (s, 1H), 7.03 (dd, J=8.2, 1.9 Hz, 1H), 7.14 (t, J=7.4 Hz, 1H), 7.26 (t, J=7.8 Hz, 1H), 7.30–7.41 (m, 8H), 7.44 (d, J=8.1 Hz, 1H), 7.61 (s, 1H), 9.50 (s, 1H); IR (KBr) 3400, 2925, 1750, 1375, 1240 and 1050 cm$^{-1}$; mass spectrum [(+) ESI], m/z 872/874 (M+H)$^+$; Anal. Calcd. for C$_{42}$H$_{46}$NClO$_{15}$: C, 57.83; H, 5.32; N, 1.61, Found: C, 57.95; H, 5.40; N, 1.62.

EXAMPLE 11

N-{5-[(4',6'-O-Benzylidene-6-deoxy-6-phenylsulfanyl-β-D-maltosyl)-oxy-methyl]-2-chloro-phenyl}-acetamide The title compound was prepared as a white solid (0.185 g, 78%) from N-{5-[(2,2',3,3'-tetra-O-acetyl-4',6'-O-benzylidene-6-deoxy-6-phenylsulfanyl-β-D-maltosyl)-oxy-methyl]-2-chloro-phenyl}-acetamide using a procedure similar to Example 2, mp 105–120° C.; $^1$H NMR (DMSO-d$_6$) δ 2.07 (s, 3H), 3.09–3.14 (m, 1H), 3.20 (dd, J=8.24, 5.49 Hz, 1H), 3.35–3.47 (m, 5H), 3.53–3.73 (m, 4H), 3.91 (dd, 1H), 4.31 (d, J=7.7 Hz, 1H), 4.54 (ABq, J=12.3 Hz, Δδ=0.06, 2H), 5.19 (d, J=4.0 Hz, 1H), 5.30–5.34 (m, 2H), 5.55–5.57 (m, 2H), 5.73 (d, J=6.4 Hz, 1H), 7.14–7.18 (m, 2H), 7.26–7.30 (m, 2H), 7.35–7.44 (m, 8H), 7.63 (s, 1H), 9.52 (s, 1H); IR (KBr 3400, 2900, 1675, 1050 cm$^{-1}$; mass spectrum [(−) FAB], m/z 702/704 (M−H)$^{-}$; Anal. Calcd. for $C_{34}H_{38}NClO_{11}S \cdot 0.5 H_2O$: C, 57.26; H, 5.51 N, 1.96, Found: C, 57.33; H, 5.40; N, 1.99.

EXAMPLE 12

N-{5-[(2,2',3,3'-Tetra-O-acetyl-4',6'-O-benzylidene-6-deoxy-6-phenylsulfinyl-β-D-maltosyl)-oxy-methyl]-2-chloro-phenyl}-acetamide The title compound was prepared as a 1:1 mixture of diastereomers, white solid (0.335 g, 69%) from N-{5-[(2,2',3,3'-tetra-O-acetyl-4',6'-O-benzylidene-6-deoxy-6-phenylsulfanyl-β-D-maltosyl)-oxy-methyl]- 2-chloro-phenyl}-acetamide using a procedure similar to Example 5, mp 160–187° C.; $^{1}$H NMR (DMSO-d$_{6}$) δ 1.91, 1.92, 1.93, 1.95, 1.96, 1.97, 1.98, 1.99, 2.00, 2.08 (10s, 15H), 3.09 (d, 1H), 3.25–3.28 (m, 1H), 3.60–4.09 (m, 4H), 4.14–4.45 (m, 2H), 4.61–4.99 (m, 5H), 5.12–5.40 (m, 3H), 5.54, 5.63 (2s, 1H), 7.04, 7.12 (2dd, 1H), 7.30–7.33 (m, 1H), 7.46–7.56 (m, 4H), 7.62, 7.68 (2s, 1H), 7.72–7.74 (m, 2H), 9.51, 9.53 (2s, 1H); IR (KBr) 3400, 2900, 1750, 1375, 1240 and 1050 cm$^{-1}$; mass spectrum [(+) FAB], m/z 888/890 (M+H)$^{+}$; Anal. Calcd. for $C_{42}H_{46}NClO_{6}S \cdot 0.5 H_2O$: C, 56.22; H, 5.28; N, 1.56, Found: C, 56.04; H, 5.21; N, 1.53.

EXAMPLE 13

N-{5-[(2,2',3,3'-Tetra-O-acetyl-4',6'-O-benzylidene-6-deoxy-6-phenethylsulfanyl-β-D-maltosyl)-oxy-methyl]-2-chloro-phenyl}-acetamide The title compound was prepared as a white solid (0.712 g, 61%) from N-(5-{[2,3,2',3'-tetra-O-acetyl-4',6'-O-benzylidene-6-O-(4-toluenesulfonyl)-β-D-maltosyl]-oxy-methyl}-2-chloro-phenyl)-acetamide using phenethylmercaptan and a procedure similar to step 8 of Example 1, mp 132–147° C.; $^{1}$H NMR (DMSO-d$_{6}$) δ 1.92 (s, 3H), 1.94 (s, 3H), 1.97 (s, 3H), 2.00 (s, 3H), 2.07 (s, 3H), 2.80–2.91 (m, 5H), 3.05 (d, 1H), 3.76–3.82 (m, 2H), 3.90–4.00 (m, 3H), 4,24 (d, J=5.5 Hz, 1H), 4.54 (d, J=12.7 Hz, 1H), 4.67–4.72 (m, 2H), 4.83–4.90 (m, 2H), 5.24–5.32 (m, 3H), 5.63 (s, 1H), 7.02 (dd, J=8.2, 1.9 Hz, 1H), 7.14–7.21 (m, 5H), 7.30–7.37 (m, 5H), 7.42 (d, J=8.3 Hz, 1H), 7.62 (s, 1H), 9.51 (s, 1H); IR (KBr) 3400, 2900, 1750, 1240 and 1050 cm$^{-1}$; mass spectrum [(+) FAB], m/z 900 (M+H)$^{+}$; Anal. Calcd. for $C_{44}H_{50}NClO_{15}S \cdot 2 H_2O$: C, 56.44; H, 5.81 N, 1.50, Found: C, 56.40; H, 5.42; N, 1.48.

EXAMPLE 14

N-{5-[(4',6'-O-Benzylidene-6-deoxy-6-phenethylsulfanyl-β-D-maltosyl)-oxy-methyl]-2-chloro-phenyl}acetamide The title compound was prepared as a white solid (0.130 g, 90%) from N-{5-[(2,2',3,3'-tetra-O-acetyl-4',6'-O-benzylidene-6-deoxy-6-phenethylsulfanyl-β-D-maltosyl)-oxy-methyl]-2-chloro-phenyl}-acetamide using a procedure similar to Example 2, mp 193–195° C.; $^{1}$H NMR (DMSO-d$_{6}$) δ 2.06 (s, 3H), 2.74 (dd, J=14.3, 7.25 Hz, 1H), 2.79–2.87 (m, 4H), 3.00 (dd, J=14.3, 2.2 Hz, 1H), 3.11 (t, J=8.35 Hz, 1H), 3.37–3.59 (m, 6H), 3.69–3.72 (m, 2H),4.08 (d, 1H), 4.32 (d, J=7.9 Hz, 1H), 4.63 4.54 (ABq, J=12.4 Hz, Δδ=0.08, 2H), 5.17 (d, J=4.0 Hz, 1H), 5.31 (br. s, 2H), 5.00 (br. s, 1H), 5.57 (s, 1H), 5.66 (br. s, 1H), 7.13–7.21 (m, 6H), 7.33–7.36 (m, 3H), 7.39–7.43 (m, 3H), 7.63 (s, 1H), 9.51 (s, 1H); IR (KBr) 3325, 2900, 1700, 1525, 1300 and 1070 cm$^{-1}$; mass spectrum [(+) FAB], m/z 754 (M+Na)$^{+}$; Anal. Calcd. for $C_{36}H_{42}NClO_{11}S$: C, 59.05; H, 5.78; N, 1.91, Found: C, 58.99; H, 5.86; N, 1.86.

EXAMPLE 15

N-(5-{[4',6'-O-Benzylidene-6-deoxy-6-(phenyl-ethyl-sulfinyl)-β-D-maltosyl]-oxy-methyl}-2-chloro-phenyl)-acetamide Step 1

N-(5-{[2,3,2',3'-Tetra-O-acetyl-4',6'-O-benzylidene-6-deoxy-6-(phenyl-ethyl-sulfinyl)-β-D-maltosyl]-oxy-methyl}-2-chloro-phenyl)-acetamide The title compound was prepared as a 1:1 mixture of diastereomers, white solid (0.189 g, 47%) from N-{5-[(2,2',3,3'-tetra-O-acetyl-4',6'-O-benzylidene-6-phenethylsulfanyl-β-D-maltosyl)-oxy-methyl]-2-chloro-phenyl}-acetamide using a procedure similar to Example 5; $^{1}$H NMR (DMSO-d$_{6}$) δ 1.94 (s, 3H), 1.95 (s, 3H), 1.96 (s, 3H), 2.00 (s, 3H), 2.09 (s, 3H), 2.96–3.29 (m, 6H), 3.76–4.46 (m, 6H), 4.50–4.79 (m, 3H), 4.88–4.94 (m, 2H), 5.23–5.40 (m, 3H), 5.63, 5.64 (2s, 1H), 7.00–7.07 (m, 1H), 7.17–7.37 (m, 10H), 7.42–7.47 (m, 1H), 7.60–7.63 (m, 1H), 9.52 (s, 1H).

Step 2

N-(5-{[4',6'-O-Benzylidene-6-(phenyl-ethyl-sulfinyl)-β-D-maltosyl]-oxy-methyl}-2-chloro-phenyl)-acetamide The title compound was prepared as a 1:1 mixture of diastereomers, white solid (0.123 g, 92%) from N-(5-{[2,3,2',3'-tetra-O-acetyl-4',6'-O-benzylidene-6-(phenyl-ethyl-sulfinyl)-β-D-maltosyl]-oxy-methyl}-2-chloro-phenyl)-acetamide using a procedure similar to Example 2, mp 202–205° C.; $^{1}$H NMR (DMSO-d$_{6}$) δ 2.07 (s, 3H), 2.97–3.16 (m, 6H), 3.28–3.76 (m, 9H), 4.14 (m, 1H), 4.38 (t, J=7.7 Hz, 1H), 4.47–4.56 (m, 3H), 4.67 (d, J=12.5 Hz, 1H), 5.16 (s, 1H), 5.36 (br. s, 2H), 5.56 (s, 2H), 5.75 (br. s, 1H), 7.14–7.19 (m, 2H), 7.24–7.26 (m, 4H), 7.33–7.39 (m, 3H), 7.41–7.43 (m, 3H), 7.57, 7.63 (2s, 1H), 9.52 (s, 1H); IR (KBr) 3400, 2900, 1670, 1425 and 1070 cm$^{-1}$; mass spectrum [(+) FAB], m/z 748 (M+H)$^{+}$; Anal. Calcd. for $C_{36}H_{42}NClO_{12}S \cdot 0.5 H_2O$: C, 57.10; H, 5.72 N, 1.85, Found: C, 57.16; H, 5.72; N, 1.79.

EXAMPLE 16

N-(5-{[4',6'-O-Benzylidene-6-deoxy-6-(3-phenyl-propylsulfanyl)-β-D-maltosyl]-oxy-methyl}-2-chloro-phenyl)-acetamide Step 1

N-(5-{[2,2',3,3'-Tetra-O-acetyl-4',6'-O-benzylidene-6-deoxy-6-(3-phenyl-propylsulfanyl)-β-D-maltosyl]-oxy-methyl}-2-chloro-phenyl)-acetamide The title compound was prepared as a white solid (0.172 g, 57%) from N-(5-{[2,3,2',3'-tetra-O-acetyl-4',6'-O-benzylidene-6-O-(4-toluenesulfonyl)-β-D-maltosyl]-oxy-methyl}-2-chloro-phenyl)-acetamide using 3-phenylpropylmercaptan and a procedure similar to step 8 of Example 1; $^{1}$H NMR (DMSO-d$_{6}$) δ 1.82–1.90 (m, 2H), 1.93 (s, 3H), 1.95 (s, 3H), 1.98 (s, 3H), 2.00 (s, 3H), 2.07 (s, 3H), 2.57–2.65 (m, 4H), 2.88 (d, 1H), 3.00 (d, 1H), 3.75–3.81 (m, 2H), 3.90–3.95 (m, 3H), 4.24 (d, J=5.4 Hz, 1H), 4.52 (d, J=12.6 Hz, 1H), 4.66–4.72 (m, 2H), 4.81–4.91 (m, 2H), 5.23–5.33 (m, 3H), 5.65 (s, 1H), 7.05 (dd, J=8.3, 1.8 Hz, 1H), 7.14–7.17 (m, 3H), 7.21–7.26 (m, 2H), 7.36 (s, 5H), 7.46 (d, J=8.3 Hz, 1H), 7.64 (s, 1H), 9.52 (s, 1H).

Step 2

N-(5-{[4',6'-O-Benzylidene-6-deoxy-6-(3-phenyl-propylsulfanyl)-β-D-maltosyl]-oxy-methyl}-2-chloro-phenyl)-acetamide The title compound was prepared as a white solid (0.161 g, 93%) from N-(5-{[2,3,2',3'-tetra-O-acetyl-4',6'-O-benzylidene-6-O-(4-toluenesulfonyl)-β-D-maltosyl]-oxy-methyl}-2-chloro-phenyl)-acetamide using a procedure similar to Example 2, mp 78–88° C.; $^1$H NMR (DMSO-d$_6$) δ 1.78–1.85 (m, 2H), 2.06 (s, 3H), 2.56 (t, J=7.2 Hz, 2H), 2.62 (t, J=7.6 Hz, 2H), 2.70 (dd, J=14.1, 7.2 Hz, 1H), 2.94 (dd, J=13.9, 2.1 Hz, 1H), 3.07–3.13 (m, 1H), 3.28–3.48 (m, 5H), 3.53–3.59 (m, 1H), 3.69 (d, J=7.2 Hz, 2H), 4.05 (d, J=5.3 Hz, 1H), 4.29 (d, 1H), 4.61 (ABq, J=12.3 Hz, Δδ=0.07, 2H), 5.15 (d, J=4.0 Hz, 1H), 5.30 (d, J=5.3 Hz, 1H), 5.33 (d, J=5.1 Hz, 1H), 5.52 (d, J=2.9 Hz, 1H), 5.57 (s, 1H), 5.70 (d, J=6.6 Hz, 1H), 7.11–7.24 (m, 6H), 7.35–7.37 (m, 3H), 7.41–7.45 (m, 3H), 7.65 (s, 1H), 9.52 (s, 1H); mass spectrum [(+) FAB], m/z 768 (M+Na)$^+$; Anal. Calcd. for C$_{37}$H$_{44}$NClO$_{11}$S.0.5 H$_2$O: C, 58.80; H, 6.01; N, 1.85, Found: C, 58.79; H, 5.95; N, 1.82.

EXAMPLE 17

N-{5-[(4',6'-O-Benzylidene-6-deoxy-6-benzoylamino-β-D-maltosyl)-oxy-methyl]-2-chloro-phenyl}-acetamide Step 1

N-{5-[(2,2',3,3'-Tetra-O-acetyl-4',6'-O-benzylidene-6-deoxy-6-amino-β-D-maltosyl)-oxy-methyl]-2-chloro-phenyl}-acetamide At ambient temperature, to a stirred solution of N-{5-[(2,2',3,3'-tetra-O-acetyl-6-deoxy-6-O-azidomethyl-4',6'-O-benzylidene-β-D-maltosyl)-oxy-methyl]-2-chloro-phenyl}-acetamide (0.371 g, 0.461 mmol) in 5% H$_2$O/THF (9.2 mL) was added triphenylphosphine (0.121 g). After 3 days, the reaction was diluted with EtOAc (50 mL), washed with brine, dried (Na$_2$SO$_4$) and concentrated. Purification on silica gel (1, 2 and 3% MeOH:CHCl$_3$ gradient) gave 0.346 g (96%) of title compound; $^1$H NMR (DMSO-d$_6$) δ 1.92 (s, 3H), 1.94 (s, 3H), 1.95 (s, 3H), 1.98 (s, 3H), 2.01 (s, 3H), 2.75 (dd, 1H), 3.00 (d, 1H), 3.33–3.64 (m, 1H), 3.78–3.95 (m, 4H), 4.23 (d, J=5.1 Hz, 1H), 4.59 (d, J=12.7 Hz, 1H), 4.67–4.82 (m, 3H), 4.88 (dd, J=10.2, 4.0 Hz, 1H), 5.20–5.30 (m, 3H), 5.65 (s, 1H), 7.09 (d, 1H), 7.38 (s, 5H), 7.47 (d, J=8.2 Hz, 1H), 7.65 (s, 1H), 9.52 (s, 1H).

Step 2

N-{5-[(2,2',3,3'-Tetra-O-acetyl-4',6'-O-benzylidene-6-deoxy-6-benzoylamino-β-D-maltosyl)-oxy-methyl]-2-chloro-phenyl}-acetamide At ambient temperature, to a stirred solution containing N-{5-[(2,2',3,3'-tetra-O-acetyl-4',6'-O-benzylidene-6-deoxy-6-amino-β-D-maltosyl)-oxy-methyl]-2-chloro-phenyl}-acetamide (0.201 g, 0.258 mmol) and pyridine (0.063 mL, 0.774 mmol) in THF (5.2 mL) was added benzoyl chloride (0.033 mL, 0.284 mmol). After 1.5 h, the reaction was quenched with H$_2$O (25 mL), extracted with EtOAc, washed successively with sat. aq. NaHCO$_3$ (3×), with sat. aq. CuSO$_4$ (3×), brine (3×), dried (Na$_2$SO$_4$) and concentrated to give 0.224 g (98%) of the title compound. This material was used without any additional purification; $^1$H NMR (DMSO-d$_6$) δ 1.94 (s, 3H), 1.96 (s, 3H), 1.99 (s, 3H), 2.02 (s, 3H), 2.07 (s, 3H), 3.39 (m, 1H), 3.76–3.79 (m, 1H), 3.89–4.00 (m, 5H), 4.20–4.24 (m, 1H), 4.55 (d, J=12.7 Hz, 1H), 4.73–4.81 (m, 3H), 4.93 (dd, J=10.2, 4.0 Hz, 1H), 5.24–5.32 (m, 3H), 5.63 (s, 1H), 6.99 (dd, J=8.2, 1.8 Hz, 1H), 7.35–7.40 (m, 6H), 7.44–7.53 (m, 3H), 7.61 (s, 1H), 7.87–7.89 (m, 2H), 8.56–8.60 (m, 1H), 9.51 (s, 1H).

Step 3

N-{5-[(4',6'-O-Benzylidene-6-deoxy-6-benzolyamino-β-D-maltosyl)-oxy-methyl]-2-chloro-phenyl}-acetamide The title compound was prepared as a white solid (0.138 g, 82%) from N-{5-[(2,2',3,3'-tetra-O-acetyl-4',6'-O-benzylidene-6-deoxy-6-benzoylamino-β-D-maltosyl)-oxy-methyl]-2-chloro-phenyl}-acetamide using a procedure similar to Example 2, mp 133–144° C.; $^1$H NMR (DMSO-d$_6$) δ 2.06 (s, 3H), 3.12–3.18 (m, 3H), 3.28–3.48 (m, 4H), 3.58–3.69 (m, 2H), 3.86–3.88 (m, 1H), 4.07–4.09 (m, 1H), 4.23–4.27 (m, 2H), 4.66 (ABq, J=12.3 Hz, Δδ=0.10, 2H), 5.16 (d, J=4.0 Hz, 1H), 5.27 (d, J=5.5 Hz, 1H), 5.36 (d, J=5.1 Hz, 1H), 5.56–5.58 (m, 2H), 5.82 (d, J=6.2 Hz, 1H), 7.12 (dd, J=8.2, 1.9 Hz, 1H), 7.34–7.50 (m, 9H), 7.62 (s, 1H), 7.82–7.85 (m, 2H), 8.47 (m, 1H), 9.51 (s, 1H). IR (KBr) 3400, 2900, 1650, 1550 and 1070 cm$^{-1}$; mass spectrum [(+) FAB], m/z 715/717 (M+H)$^+$; Anal. Calcd. for C$_{35}$H$_{39}$N$_2$ClO$_{12}$: C, 58.78; H, 5.50; N, 3.92, Found: C, 58.49; H, 5.60; N, 3.73.

EXAMPLE 18

N-(5-{[4',6'-O-Benzylidene-6-deoxy-6-(2-phenyl-1-oxo-ethyl-amino)-β-D-maltosyl]-oxy-methyl}-2-chloro-phenyl)-acetamide Step 1

N-(5-{[2,2',3,3'-Tetra-O-acetyl-4',6'-O-benzylidene-6-deoxy-6-(2-phenyl-1-oxo-ethyl-amino)-β-D-maltosyl]-oxy-methyl}-2-chloro-phenyl)-acetamide The title compound was prepared as a solid (0.176 g, 94%) from N-{5-[(2,2',3,3'-tetra-O-acetyl-4',6'-O-benzylidene-6-deoxy-6-amino-β-D-maltosyl)-oxy-methyl]-2-chloro-phenyl}-acetamide using phenylacetyl chloride and a procedure similar to step 2 of Example 17; $^1$H NMR (DMSO-d$_6$) δ 1.93 (s, 3H), 1.95 (s, 3H), 1.97 (s, 3H), 2.00 (s, 3H), 2.09 (s, 3H), 3.20 (m, 1H), 3.50 (s, 2H), 3.70–3.92 (m, 6H), 4.18–4.20 (m, 1H), 4.48 (d, J=12.6 Hz, 1H), 4.71–4.77 (m, 3H), 4.90 (dd, J=10.2, 4.1 Hz, 1H), 5.19–5.28 (m, 3H), 5.61 (s, 1H), 7.04 (dd, J=8.3, 1.6 Hz, 1H), 7.19–7.30 (m, 5H), 7.37 (s, 5H), 7.47 (d, J=8.3 Hz, 1H), 7.64 (s, 1H), 8.16 (s, 1H), 9.54 (s, 1H).

Step 2

N-(5-{[4',6'-O-Benzylidene-6-deoxy-6-(2-phenyl-1-oxo-ethyl-amino)-β-D-maltosyl]-oxy-methyl}-2-chloro-phenyl)-acetamide The title compound was prepared as a white solid (0.109 g, 85%) from N-(5-{[2,2',3,3'-tetra-O-acetyl-4',6'-O-benzylidene-6-deoxy-6-(2-phenyl-1-oxo-ethyl-amino)-β-D-maltosyl]-oxy-methyl}-2-chloro-phenyl)-acetamide using a procedure similar to Example 2, mp 115° C.; $^1$H NMR (DMSO-d$_6$) δ 2.09 (s, 3H), 2.90–2.95 (m, 1H), 3.09–3.14 (m, 1H), 3.25–3.50 (m, 7H), 3.53–3.63 (m, 2H), 3.73–3.79 (m, 1H), 3.90 (dd, J=13.0, 6.8 Hz, 1H), 4.20–4.23 (m, 2H), 4.63 (ABq, J=12.5 Hz, Δδ=0.13, 2H), 5.08 (d, J=3.7 Hz, 1H), 5.26 (d, J=5.3 Hz, 1H), 5.34 (d, J=5.1 Hz, 1H), 5.52 (d, J=2.9 Hz, 1H), 5.55 (s, 1H), 5.78 (d, J=6.4 Hz, 1H), 7.15–7.27 (m, 6H), 7.34–7.37 (m, 3H), 7.41–7.46 (m, 3H), 7.66 (s, 1H), 8.01–8.03 (m, 1H), 9.54 (s, 1H). IR (KBr) 3375, 2900, 1650, 1540 and 1070 cm$^{-1}$; mass spectrum [(+) FAB], m/z 729 (M+H)$^+$; Anal. Calcd. for C$_{36}$H$_{41}$N$_2$ClO$_{12}$.H$_2$O: C, 57.87; H, 5.80; N, 3.75, Found: C, 57.87; H, 5.66; N, 3.66.

EXAMPLE 19

N-{5-[(4',6'-O-Benzylidene-6-deoxy-6-phenethylsulfanyl-β-D-maltosyl)-oxy-methyl]-2-chloro-phenyl}-carbamic acid methyl ester Step 1

N-{5-[(Hepta-O-acetyl-β-D-maltosyl)-oxymethyl]-2-chloro-phenyl}-carbamic acid methyl ester To a stirred solution of 2-chloro-5-(hepta-O-acetyl-β-D-maltosyl-oxymethyl)-phenylamine (1.40 g, 1.80 mmol) in THF (18 mL) at 0° C. was added NaH (0.108 g, 2.70 mmol). After 10 min. at this temperature, methyl chloroformate (0.167 mL, 2.16 mmol) was added, and then the reaction was warmed to rt for 3 h. At this point, the reaction was concentrated, and the residue was diluted with EtOAc (300 mL). This solution was washed with 1N HCl (30 mL), sat. aq. NaHCO$_3$ (30 mL), and brine (30 mL) and then dried (MgSO$_4$). After concentration, the resulting oilly residue was purified by flash chromatography (2:98 to 10:90 acetone:CHCl$_3$ gradient) to afford the product (1.33 g, 88%) as a white foam, mp >79° C. (decomp.); $^1$H NMR (DMSO-d$_6$) δ 1.93 (s, 3H), 1.94 (s, 6H), 1.970 (s, 3H), 1.973 (s, 3H), 2.01 (s, 3H), 2.08 (s, 3H), 3.64 (s, 3H), 3.91–4.03 (m, 4H), 4.12–4.23 (m, 2H), 4.38 (dd, J=1.8, 11.9 Hz, 1H), 4.54 (d, J=12.7 Hz, 1H), 4.69–4.75 (m, 2H), 4.83–4.88 (m, 2H), 4.97 (t, J=9.7 Hz, 1H), 5.21 (dd, J=9.7, 10.3 Hz, 1H), 5.27 (d, J=3.7 Hz, 1H), 5.30 (dd, J=8.6, 9.2 Hz, 1H), 7.07 (dd, J=2.0, 8.3 Hz, 1H), 7.44 (d, J=8.1 Hz, 1H), 7.48 (d, J=1.8 Hz, 1H), 9.08 (s, 1H); IR (KBr) 3420, 2950, 1755, 1590, 1530, 1450, 1420, 1375, 1230, 1130, and 1040 cm$^{-1}$; mass spectrum [(+) FAB], m/z 834 (M+H)$^+$, 856 (M+Na)$^+$, Anal. Calcd. for C$_{35}$H$_{44}$ClNO$_{20}$.0.5 H$_2$O: C, 49.86; H, 5.38; N, 1.66, Found: C, 49.68; H, 5.14; N, 1.58.

Step 2

{2-Chloro-5-[(β-D-maltosyl)-oxy-methyl]-phenyl}-carbamic acid methyl ester

The title compound was prepared as a white foam (0.753 g, 99%) from N-{5-[(hepta-O-acetyl-β-D-maltosyl)-oxymethyl]-2-chloro-phenyl}-carbamic acid methyl ester using a procedure similar to Example 2, mp >109° C. (decomp.); $^1$H NMR (DMSO-d$_6$) δ 3.01–3.11 (m, 2H), 3.19–3.27 (m, 2H), 3.28–3.38 (m, 2H), 3.38–3.50 (m, 3H), 3.52–3.64 (m, 2H), 3.64 (s, 3H), 3.72 (d, J=11.2 Hz, 1H), 4.28 (d, J=7.9 Hz, 1H), 4.44–4.57 (m, 2H), 4.67 (ABq, J=12.5 Hz, Δδ=0.22, 2H), 4.83–4.96 (bs, 2H), 5.01 (d, J=4.0 Hz, 1H), 5.16–5.32 (bs, 1H), 5.34–5.58 (bs, 2H), 7.21 (dd, J=2.0, 8.1 Hz, 1H), 7.43 (d, J=8.1 Hz, 1H), 7.53 (d, J=1.8 Hz, 1H), 9.07 (s, 1H; IR (KBr) 3420, 2920, 1725, 1590, 1530, 1450, 1425, 1370, 1310, 1255, 1230, 1140, 1070, and 1030 cm$^{-1}$; mass spectrum [(+) FAB], m/z 562/564 (M+Na)$^+$, Anal. Calcd. for C$_{21}$H$_{30}$ClNO$_{13}$.0.5 H$_2$O: C, 45.95; H, 5.69; N, 2.55, Found: C, 45.81; H, 5.82; N, 2.39.

Step 3

N-{5-[(4',6'-O-Benzylidene-β-D-maltosyl)-oxy-methyl]-2-chloro-phenyl}-carbamic acid methyl ester The title compound was prepared as a white solid (0.552 g, 71%) from {2-chloro-5-[(β-D-maltosyl)-oxy-methyl]-phenyl}-carbamic acid methyl ester using a procedure similar to step 5 of Example 1, mp 142–145° C.; $^1$H NMR (DMSO-d$_6$) δ 3.06–3.13 (m, 1H), 3.28–3.41 (m, 4H), 3.46 (td, J=2.4, 8.8 Hz, 1H), 3.50–3.61 (m, 2H), 3.65 (s, 3H), 3.65–3.75 (m, 3H), 4.11 (dd, J=3.1, 8.1 Hz, 1H), 4.30 (d, J=7.7 Hz, 1H), 4.64–4.69 (m, 1H), 4.68 (ABq, J=12.5 Hz, Δδ=0.22, 2H), 5.14 (d, J=3.7 Hz, 1H), 5.26 (d, J=5.1 Hz, 1H), 5.30 (d, J=4.8 Hz, 1H), 5.51 (d, J=2.9 Hz, 1H), 5.57 (s, 1H), 5.63 (d, J=6.4 Hz, 1H), 7.22 (dd, J=2.0, 8.1 Hz, 1H), 7.34–7.38 (m, 3H), 7.41–7.46 (m, 3H), 7.54 (d, J=1.8 Hz, 1H), 9.07 (s, 1H); IR (KBr) 3530, 3410, 2920, 2850, 1730, 1590, 1535, 1450, 1420, 1375, 1310, 1250, 1230, 1145, 1075, 1030, and 1000 cm$^{-1}$; mass spectrum [(+) FAB], m/z 650/652 (M+Na)$^+$; Anal. Calcd. for C$_{28}$H$_{34}$ClNO$_{13}$.0.5 H$_2$O: C, 52.79; H, 5.54; N, 2.20, Found: C, 52.85; H, 5.77; N, 2.11.

Step 4

N-(5-{[4',6'-O-Benzylidene-6-O-(4-toluenesulfonyl)-β-D-maltosyl]-oxy-methyl}-2-chloro-phenyl)-carbamic acid methyl ester The title compound was prepared as a white solid (0.686 g, 70%) from N-{5-[(4',6'-O-benzylidene-β-D-maltosyl)-oxy-methyl]-2-chloro-phenyl}-carbamic acid methyl ester using a procedure similar to step 6 of Example 1; $^1$H NMR (DMSO-d$_6$) δ 2.34 (s, 3H), 3.11 (t, 1H), 3.36–3.67 (m, 1H), 3.96 (d, J=5.1 Hz, 1H), 4.14 (dd, 1H), 4.30–4.35 (m, 2H), 4.56 (ABq, J=12.4 Hz, Δδ=0.06, 2H), 5.07 (d, J=3.7 Hz, 1H), 5.36 (br. s, 2H), 5,58 (s, 2H), 5.77 (br. s, 1H), 7.20 (dd, J=8.3, 2.0 Hz, 1H), 7.37–7.53 (m, 9H), 7.80 (d, J=8.4 Hz, 2H), 9.10 (s, 1H).

Step 5

N-(5-{[2,2',3,3'-Tetra-O-acetyl-4',6'-O-benzylidene-6-O-(4-toluenesulfonyl)-β-D-maltosyl]-oxy-methyl}-2-chloro-phenyl)-carbamic acid methyl ester The title compound was prepared as a white solid (0.812 g, 99%) from N-(5-{[4',6'-O-benzylidene-6-O-(4-toluenesulfonyl)-β-D-maltosyl]-oxy-methyl}-2-chloro-phenyl)-carbamic acid methyl ester using a procedure similar to step 7 of Example 1; $^1$H NMR (DMSO-d$_6$) δ 1.92 (s, 3H), 1.93 (s, 3H), 1.97 (s, 3H), 2.01 (s, 3H), 2.30 (s, 3H), 3.66 (s, 3H), 3.69–4.04 (m, 5H), 4.19–4.22 (m, 1H), 4.23–4.43 (m, 3H), 4.56–4.65 (m, 2H), 4,80 (d, J=8.1 Hz, 1H), 4.88 (dd, J=10.2, 4.1 Hz, 1H), 5.18–5.33 (m, 3H), 5.66 (s, 1H), 7.05 (dd, J=8.3, 1.8 Hz, 1H), 7.30–7.48 (m, 9H), 7.82 (d, J=8.4 Hz, 2H), 9.11 (s, 1H).

Step 6

N-{5-[(2,2',3,3'-Tetra-O-acetyl-4',6'-O-benzylidene-6-deoxy-6-phenethylsulfanyl-β-D-maltosyl)-oxy-methyl]-2-chloro-phenyl}-carbamic acid methyl ester The title compound was prepared as a white solid (0.217 g, 82%) from N-(5-{[2,2',3,3'-tetra-O-acetyl-4',6'-O-benzylidene-6-O-(4-toluenesulfonyl)-β-D-maltosyl]-oxy-methyl}-2-chloro-phenyl)-carbamic acid methyl ester using a procedure similar to step 8 of Example 1; $^1$H NMR (DMSO-d$_6$) δ 1.93 (s, 3H), 1.95 (s, 3H), 1.98 (s, 3H), 2.01 (s, 3H), 2.81–2.93 (m, 5H), 3.04–3.09 (m, 1H), 3.65 (s, 3H), 3.78–3.85 (m, 2H), 3.90–3.97 (m, 3H), 4.24–4.26 (m, 1H), 4.56 (d, J=12.7 Hz, 1H), 4.68–4.74 (m, 2H), 4.84–4.92 (m, 2H), 5.24–5.34 (m, 3H), 5.65 (s, 1H), 7.04 (dd, J=8.3, 1.7 Hz, 1H), 7.14–7.30 (m, 5H), 7.30–7.40 (m, 5H), 7.42 (d, J=8.2 Hz, 1H), 7.48 (s, 1H), 9.10 (s, 1H).

Step 7

N-{5-[(4',6'-O-Benzylidene-6-deoxy-6-phenethylsulfanyl-β-D-maltosyl)-oxy-methyl]-2-chloro-phenyl}-carbamic acid methyl ester The title compound was prepared as a white solid (0.135 g, 79%) from N-{5-[(2,2',3,3'-tetra-O-acetyl-4',6'-O-benzylidene-6-deoxy-6-phenethylsulfanyl-β-D-maltosyl)-oxy-methyl]-2-chloro-phenyl}-carbamic acid methyl ester using a procedure similar to Example 2, mp 85–90° C.; $^1$H NMR (DMSO-d$_6$) δ 2.74 (dd, J=14.2, 7.1 Hz, 1H), 2.81–2.86 (m, 4H), 3.00 (dd, J=14.2, 2.1 Hz, 1H), 3.09–3.14 (m, 1H), 3.37–3.47 (m, 4H), 3.51–3.59 (m, 2H), 3.64 (s, 3H), 3.69–3.72 (m, 2H), 4.08–4.09 (m, 1H), 4.32 (d, J=7.9 Hz, 1H), 4.63 (ABq, J=12.3 Hz, Δδ=0.07, 2H), 5.17 (d, J=3.7 Hz, 1H), 5.31 (t, J=5.7 Hz, 2H), 5.50 (d, J=3.1 Hz, 1H), 5.57 (s, 1H), 5.66 (d, J=6.6 Hz, 1H), 7.13–7.21 (m, 6H), 7.33–7.36 (m, 3H), 7.39–7.43 (m, 3H), 7.51 (d, J=1.8 Hz, 1H), 9.06 (s, 1H); IR (KBr) 3400, 2900, 1740, 1540 and 1070 cm$^{-1}$; mass spectrum [(−) FAB], m/z 746 (M−H)$^-$; Anal. Calcd. for $C_{36}H_{42}NClO_{12}S \cdot 0.5\ H_2O$: C, 57.10; H, 5.72; N, 1.85, Found: C, 57.14; H, 5.53; N, 1.86.

EXAMPLE 20

N-{5-[(4',6'-O-Benzylidene-6-deoxy-6-benzylsulfinyl-β-D-maltosyl)-oxy-methyl]-2-chloro-phenyl}-carbamic acid methyl ester Step 1

N-{5-[2,2',3,3'-Tetra-O-acetyl-4',6'-O-benzylidene-6-deoxy-6-benzylsulfanyl-β-D-maltosyl)-oxy-methyl]-2-chloro-phenyl}-carbamic acid methyl ester The title compound was prepared as a white solid (0.343 g, 66%) from N-(5-{[2,2',3,3'-tetra-O-acetyl-4',6'-O-benzylidene-6-O-(4-toluenesulfonyl)-β-D-maltosyl]-oxy-methyl}-2-chloro-phenyl)-carbamic acid methyl ester using benzyl mercaptan and a procedure similar to step 8 of Example 1; $^1$H NMR (DMSO-d$_6$) δ 1.92 (s, 3H), 1.95 (s, 3H), 1.97 (s, 3H), 2.02 (s, 3H), 2.75–2.80 (m, 1H), 2.90 (d, J=13.0 Hz, 1H), 3.65 (s, 3H), 3.69–3.94 (m, 7H), 4.18–4.22 (m, 1H), 4.60 (d, J=12.7 Hz, 1H), 4.69–4.91 (m, 4H), 5.21–5.32 (m, 3H), 5.65 (s, 1H), 7.10 (dd, J=8.2, 1.8 Hz, 1H), 7.16–7.21 (m, 1H), 7.27–7.41 (m, 9H), 7.46 (d, J=8.2 Hz, 1H), 7.52 (s, 1H), 9.10 (s, 1H).

Step 2

N-{5-[(2,2',3,3'-Tetra-O-acetyl-4',6'-O-benzylidene-6-deoxy-6-benzylsulfinyl -β-D-maltosyl)-oxy-methyl]-2-chloro-phenyl}-carbamic acid methyl ester The title compound was prepared as a 1:1 mixture of diastereomers, white solid (0.289 g, 89%) from N-{5-[(2,2',3,3'-tetra-O-acetyl-4',6'-O-benzylidene-6-deoxy-6-benzylsulfanyl-β-D-maltosyl)-oxy-methyl]-2-chloro-phenyl}-carbamic acid methyl ester using a procedure similar to Example 5; $^1$H NMR (DMSO-d$_6$) δ 1.92, 1.93, 1.94, 1.95, 1.96, 1.98, 2.01, 2.09 (8s, 12H), 3.08–3.15 (m, 2H), 3.65 (s, 3H), 3.76–3.81 (m, 2H), 3.82–3.97 (m, 2H), 4.01–4.10 (m, 2H), 4.22–4.33 (m, 2H), 4.58–4.62 (m, 1H), 4.71–4.96 (m, 4H), 5.23–5.33 (m, 3H), 5.65, 5.69 (2s, 1H), 7.08 (dd, 1H), 7.28–7.51 (m, 12H), 9.10 (s, 1H).

Step 3

N-{5-[(4',6'-O-Benzylidene-6-deoxy-6-benzylsulfinyl-β-D-maltosyl)-oxy-methyl]-2-chloro-phenyl}-carbamic acid methyl ester The title compound was prepared as a 1:1 mixture of diastereomers, white solid (0.212 g, 95%) from N-{5-[(2,2',3,3'-tetra-O-acetyl-4',6'-O-benzylidene-6-deoxy-6-benzylsulfinyl -β-D-maltosyl)-oxy-methyl]-2-chloro-phenyl}-carbamic acid methyl ester using a procedure similar to Example 2, mp 119–128° C.; $^1$H NMR (DMSO-d$_6$) δ 2.97–3.02 (m, 1H), 3.11–3.19 (m, 1H), 3.25–3.72 (m, 11H), 3.87–3.98 (m, 2H), 4.05–4.10 (m, 1H), 4.21 (d, J=12.7 Hz, 1H), 4.35, 4.44 (2d, 1H), 4.59 (dd, 1H), 4.74 (t, J=12.3 Hz, 1H), 5.19 (t, J=4.5 Hz, 1H), 5.33–5.39 (m, 2H), 5.56–5.59 (m, 2H), 5.67, 5.75 (2d, 1H), 7.18–7.21 (m, 1H), 7.28–7.48 (m, 11H), 7.53–7.54 (m, 1H), 9.06 (s, 1H); IR (KBr) 3400, 2925, 1735, 1590, 1540 and 1075 cm$^{-1}$; mass spectrum [(+) FAB], m/z 772 (M+Na)$^+$; Anal. Calcd. for $C_{35}H_{40}NClO_{13}S$: C, 56.04; H, 5.37; N, 1.87, Found: C, 55.94; H, 5.39; N, 1.82.

What is claimed is:

1. A compound of formula I having the structure

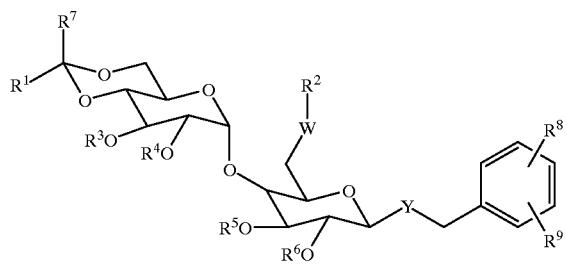

I wherein

W is S, SO, SO$_2$, NR;

Y is O, S, NR, or CH$_2$;

R is hydrogen or alkyl of 1–6 carbon atoms, perfluoroalkyl of 1–6 carbon atoms, acyl of 2–7 carbon atoms, perfluoroacyl of 2–7 carbon atoms;

R$^1$ and R$^7$ are each, independently, alkyl of 1–6 carbon atoms, perfluoroalkyl of 1–6 carbon atoms, haloalkyl of 1–6 carbon atoms, nitroalkyl of 1–6 carbon atoms, cyanoalkyl of 1–6 carbon atoms, alkoxyalkyl of 2–12 carbon atoms, nitriloalkyl of 1–6 carbon atoms, phenyl mono-, di-, or tri-substituted with R$^8$, phenylalkyl of 7–10 carbon atoms, wherein the phenyl ring is mono-, di-, or tri-substituted with R$^8$, pyridyl substituted with R$^8$, furyl substituted with R$^8$, thienyl substituted with R$^8$, and thiazolyl substituted with R$^8$;

R$^2$ is hydrogen,

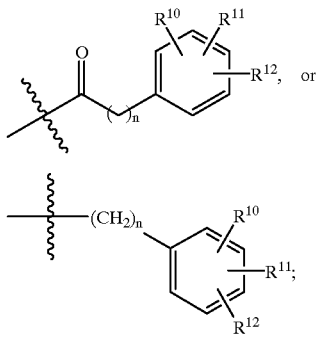

R$^3$, R$^4$, R$^5$, and R$^6$ are each, independently, hydrogen, acyl of 2–7 carbon atoms, perfluoroacyl of 2–7 carbon atoms, alkyl of 1–6 carbon atoms, perfluoroalkyl of 1–6 carbon atoms, benzyl, wherein the phenyl moiety is mono-, di-, or tri-substituted with R$^8$, benzoyl, wherein the phenyl moiety is mono-, di-, or tri-substituted with R$^8$;

R$^8$ is hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —NO$_2$, halogen, or —CF$_3$;

R$^9$ is hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —NO$_2$, halogen, —NHCO$_2$R$^{13}$, —NHSO$_2$R$^{13}$, —NR$^{14}$R$^{15}$,

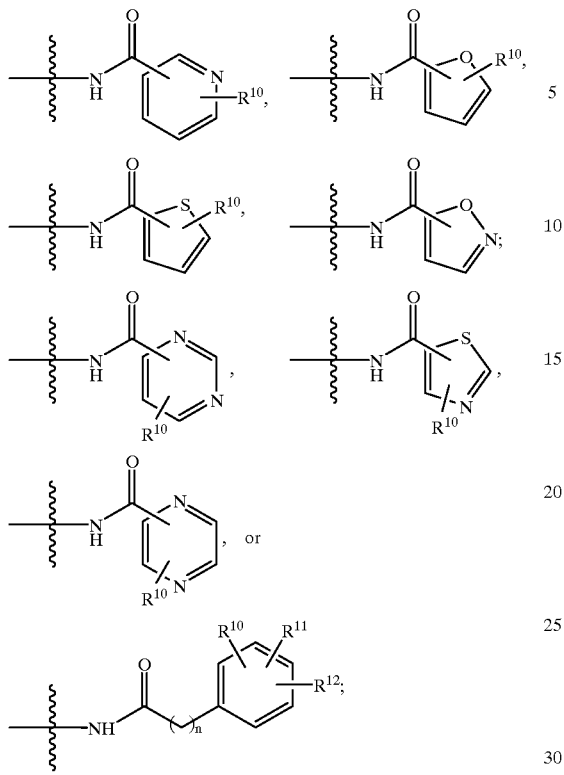

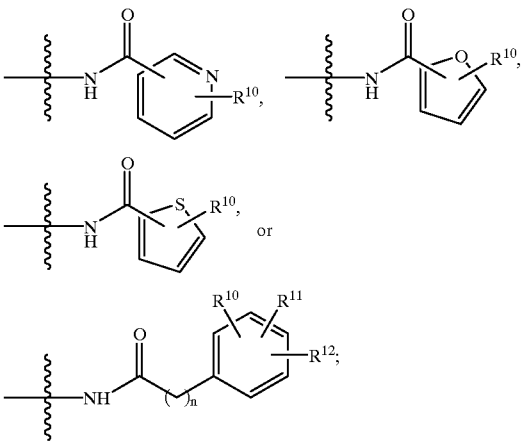

$R^{10}$, $R^{11}$, and $R^{12}$, are each, independently, hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —NO$_2$, halogen, acyl of 2–7 carbon atoms, perfluoroacyl of 2–7 carbon atoms, or benzoyl, wherein the phenyl moiety of the benzoyl group is optionally mono-, di-, or tri-substituted with alkyl of 1–6 carbon atoms, alkoxy of 1–6 carbon atoms, —CN, —NO$_2$, halogen, or —CF$_3$;

$R^{13}$ is alkyl of 1–6 carbon atoms, perfluoroalkyl of 1–6 carbon atoms, phenyl or phenyl substituted with halogen;

$R^{14}$ and $R^{15}$ are each, independently, hydrogen, alkyl of 1–6 carbon atoms, perfluoroalkyl of 1–6 carbon atoms, acyl of 2–7 carbon atoms, perfluoroacyl of 2–7 carbon atoms;

n=0–3;

or a pharmaceutically acceptable salt thereof.

2. The compound according to claim 1, wherein

Y is O;

$R^3$, $R^4$, $R^5$, and $R^6$ are each, independently, hydrogen, or acyl of 2–7 carbon atoms;

$R^9$ is hydrogen, alkyl of 1–6 carbon atoms, alkoxy of 1–6 carbon atoms, phenyl, —CN, —NO$_2$, halogen, —CF$_3$, —NHR$^3$, —NR$^3$R$^3$, —NR$^3$R$^3$, —NHCO$_2$R$^{13}$, —NHSO$_2$R$^{13}$, or a pharmaceutically acceptable salt thereof.

3. The compound according to claim 2, wherein
$R^1$ is phenyl mono-, di-, or tri-substituted with $R^8$;
or a pharmaceutically acceptable salt thereof.

4. The compound of claim 1, which is N-{5-[(2,3,2',3'-Tetra-O-acetyl-6-deoxy-6-benzylsulfanyl-4',6'-O-benzylidene-β-D-maltosyl)-oxy-methyl]-2-chloro-phenyl}-acetamide or a pharmaceutically acceptable salt thereof.

5. The compound of claim 1, which is N-{5-[(4',6'-O-Benzylidene-6-deoxy-6-benzylsulfanyl-βD-maltosyl)-oxy-methyl]-2-chloro-phenyl}-acetamide or a pharmaceutically acceptable salt thereof.

6. The compound of claim 1, which is N-(5-{[2,3,2',3'-Tetra-O-acetyl-6-deoxy-6-(2,4-dichloro-benzylsulfanyl)-4',6'-O-benzylidene-βD-maltosyl]-oxy-methyl}-2-chloro-phenyl)-acetamide or a pharmaceutically acceptable salt thereof.

7. The compound of claim 1, which is N-(5-{[4',6'-O-Benzylidene-6-deoxy-6-(2,4-dichloro-benzylsulfanyl)-β-D-maltosyl]-oxy-methyl}-2-chloro-phenyl)-acetamide or a pharmaceutically acceptable salt thereof.

8. The compound of claim 1, which is N-{5-[(2,3,2',3'-Tetra-O-acetyl-4',6'-O-benzylidene-6-deoxy-6-benzylsulfinyl-β-D-maltosyl)-oxy-methyl]-2-chloro-phenyl}-acetamide or a pharmaceutically acceptable salt thereof.

9. The compound of claim 1, which is N-{5-[(4',6'-O-Benzylidene-6-deoxy-6-benzylsulfinyl-β-D-maltosyl)-oxy-methyl]-2-chloro-phenyl}-acetamide or a pharmaceutically acceptable salt thereof.

10. The compound of claim 1, which is N-{5-[(4',6'-O-Benzylidene-6-deoxy-6-benzylsulfonyl-β-D-maltosyl)-oxy-methyl]-2-chloro-phenyl}-acetamide or a pharmaceutically acceptable salt thereof.

11. The compound of claim 1, which is N-{5-[(2,2',3,3'-Tetra-O-acetyl-4',6'-O-benzylidene-6-deoxy-6-phenylsulfanyl-β-D-maltosyl)-oxy-methyl]-2-chloro-phenyl}-acetamide or a pharmaceutically acceptable salt thereof.

12. The compound of claim 1, which is N-{5-[(4',6'-O-Benzylidene-6-deoxy-6-phenylsulfanyl-β-D-maltosyl)-oxy-methyl]-2-chloro-phenyl}-acetamide or a pharmaceutically acceptable salt thereof.

13. The compound of claim 1, which is N-{5-[(2,2',3,3'-Tetra-O-acetyl-4',6'-O-benzylidene-6-deoxy-6-phenylsulfinyl-β-D-maltosyl)-oxy-methyl]-2-chloro-phenyl}-acetamide or a pharmaceutically acceptable salt thereof.

14. The compound of claim 1, which is N-{5-[(4',6'-O-Benzylidene-6-deoxy-6-phenethylsulfanyl-β-D-maltosyl)-oxy-methyl]-2-chloro-phenyl}acetamide or a pharmaceutically acceptable salt thereof.

15. The compound of claim 1, which is N-{5-[(2,2',3,3'-Tetra-O-acetyl-4',6'-O-benzylidene-6-deoxy-6-phenethylsulfanyl-β-D-maltosyl)-oxy-methyl]-2-chloro-phenyl}-acetamide or a pharmaceutically acceptable salt thereof.

16. The compound of claim 1, which is N-(5-{[4',6'-O-Benzylidene-6-deoxy-6-(phenyl-ethyl-sulfinyl)-β-D-maltosyl]-oxy-methyl}-2-chloro-phenyl)-acetamide or a pharmaceutically acceptable salt thereof.

17. The compound of claim 1, which is N-(5-{[4',6'-O-Benzylidene-6-deoxy-6-(3-phenyl-propylsulfanyl)-β-D-maltosyl]-oxy-methyl}-2-chloro-phenyl)-acetamide or a pharmaceutically acceptable salt thereof.

18. The compound of claim 1, which is N-{5-[(4',6'-O-Benzylidene-6-deoxy-6-benzoylamino-β-D-maltosyl)-oxy-methyl]-2-chloro-phenyl}-acetamide or a pharmaceutically acceptable salt thereof.

19. The compound of claim 1, which is N-(5-{[4',6'-O-Benzylidene-6-deoxy-6-(2-phenyl-1-oxo-ethyl-amino)-β-D-maltosyl]-oxy-methyl}-2-chloro-phenyl)-acetamide or a pharmaceutically acceptable salt thereof.

20. The compound of claim 1, which is N-{5-[(4',6'-O-Benzylidene-6-deoxy-6-phenethylsulfanyl-β-D-maltosyl)-oxy-methyl]-2-chloro-phenyl}-carbamic acid methyl ester or a pharmaceutically acceptable salt thereof.

21. The compound of claim 1, which is N-{5-[(4',6'-O-Benzylidene-6-deoxy-6-benzylsulfinyl-β-D-maltosyl)-oxy-methyl]-2-chloro-phenyl}-carbamic acid methyl ester or a pharmaceutically acceptable salt thereof.

22. A method of treating or inhibiting hyperproliferative vascular disorders in a mammal in need thereof, which comprises administering to said mammal an effective amount of a compound of formula I having the structure

I

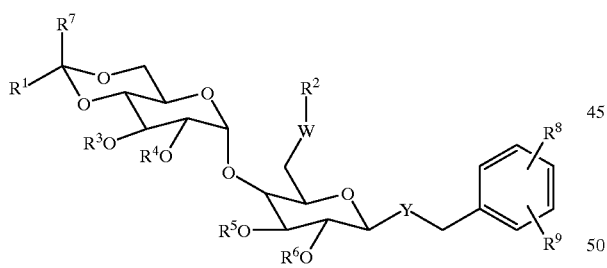

wherein

W is S, SO, SO$_2$, NR;

Y is O, S, NR, or CH$_2$;

R is hydrogen or alkyl of 1–6 carbon atoms, perfluoroalkyl of 1–6 carbon atoms, acyl of 2–7 carbon atoms, perfluoroacyl of 2–7 carbon atoms;

R$^1$ and R$^7$ are each, independently, alkyl of 1–6 carbon atoms, perfluoroalkyl of 1–6 carbon atoms, haloalkyl of 1–6 carbon atoms, nitroalkyl of 1–6 carbon atoms, cyanoalkyl of 1–6 carbon atoms, alkoxyalkyl of 2–12 carbon atoms, nitriloalkyl of 1–6 carbon atoms, phenyl mono-, di-, or tri-substituted with R$^8$, phenylalkyl of 7–10 carbon atoms, wherein the phenyl ring is mono-, di-, or tri-substituted with R$^8$, pyridyl substituted with R$^8$, furyl substituted with R$^8$, thienyl substituted with R$^8$, and thiazolyl substituted with R$^8$;

R$^2$ is hydrogen,

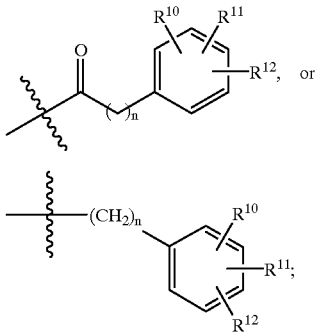

R$^3$, R$^4$, R$^5$, and R$^6$ are each, independently, hydrogen, acyl of 2–7 carbon atoms, perfluoroacyl of 2–7 carbon atoms, alkyl of 1–6 carbon atoms, perfluoroalkyl of 1–6 carbon atoms, benzyl, wherein the phenyl moiety is mono-, di-, or tri-substituted with R$^8$, benzoyl, wherein the phenyl moiety is mono-, di-, or tri-substituted with R$^8$;

R$^8$ is hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —NO$_2$, halogen, or —CF$_3$;

R$^9$ is hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —NO$_2$, halogen, —NHCO$_2$R$^{13}$, —NHSO$_2$R$^{13}$, —NR$^{14}$R$^{15}$,

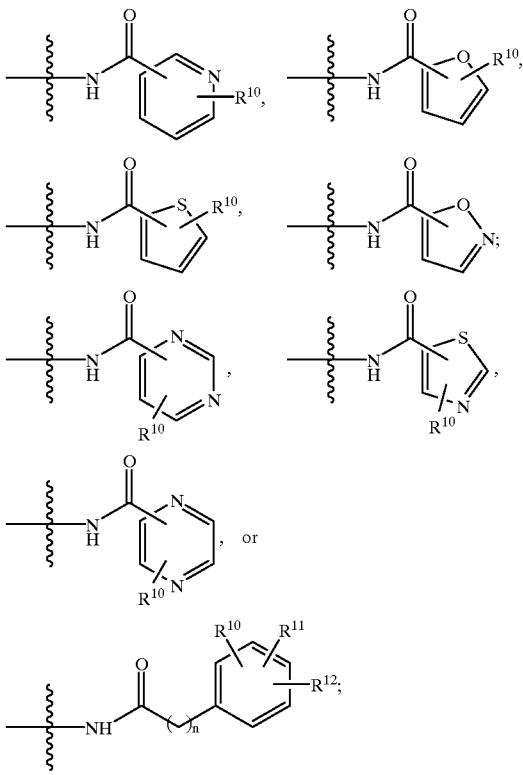

R$^{10}$, R$^{11}$, and R$^{12}$, are each, independently, hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —NO$_2$, halogen, acyl of 2–7 carbon atoms, perfluoroacyl of 2–7 carbon atoms, or benzoyl, wherein the phenyl moiety of the benzoyl group is optionally mono-, di-, or tri-substituted with alkyl of 1–6 carbon atoms, alkoxy of 1–6 carbon atoms, —CN, —NO$_2$, halogen, or —CF$_3$;

$R^{13}$ is alkyl of 1–6 carbon atoms, perfluoroalkyl of 1–6 carbon atoms, phenyl or phenyl substituted with halogen;

$R^{14}$ and $R^{15}$ are each, independently, hydrogen, alkyl of 1–6 carbon atoms, perfluoroalkyl of 1–6 carbon atoms, acyl of 2–7 carbon atoms, perfluoroacyl of 2–7 carbon atoms;

n=0–3;

or a pharmaceutically acceptable salt thereof.

23. The method according to claim 22, wherein the restenosis results from a vascular angioplasty procedure, vascular reconstructive surgery, or organ or tissue transplantation.

24. A method of inhibiting angiogenesis in a malignant tumor, sarcoma, or neoplastic tissue in a mammal in need thereof, which comprises administering to said mammal an effective amount of a compound of formula I having the structure

I

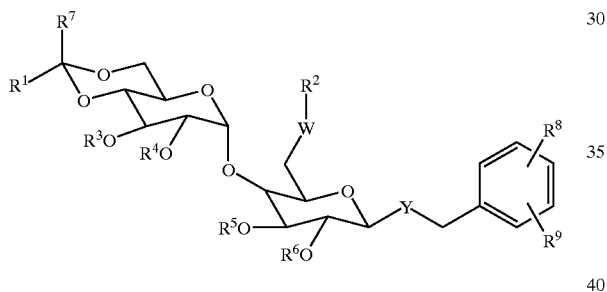

wherein

W is S, SO, SO$_2$, NR;

Y is O, S, NR, or CH$_2$;

R is hydrogen or alkyl of 1–6 carbon atoms, perfluoroalkyl of 1–6 carbon atoms, acyl of 2–7 carbon atoms, perfluoroacyl of 2–7 carbon atoms;

$R^1$ and $R^7$ are each, independently, alkyl of 1–6 carbon atoms, perfluoroalkyl of 1–6 carbon atoms, haloalkyl of 1–6 carbon atoms, nitroalkyl of 1–6 carbon atoms, cyanoalkyl of 1–6 carbon atoms, alkoxyalkyl of 2–12 carbon atoms, nitriloalkyl of 1–6 carbon atoms, phenyl mono-, di-, or tri-substituted with $R^8$, phenylalkyl of 7–10 carbon atoms, wherein the phenyl ring is mono-, di-, or tri-substituted with $R^8$, pyridyl substituted with $R^8$, furyl substituted with $R^8$, thienyl substituted with $R^8$, and thiazolyl substituted with $R^8$;

$R^2$ is hydrogen,

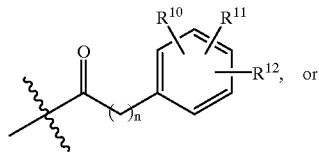

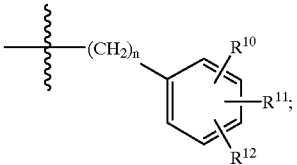

$R^3$, $R^4$, $R^5$, and $R^6$ are each, independently, hydrogen, acyl of 2–7 carbon atoms, perfluoroacyl of 2–7 carbon atoms, alkyl of 1–6 carbon atoms, perfluoroalkyl of 1–6 carbon atoms, benzyl, wherein the phenyl moiety is mono-, di-, or tri-substituted with $R^8$, benzoyl, wherein the phenyl moiety is mono-, di-, or tri-substituted with $R^8$;

$R^8$ is hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —NO$_2$, halogen, or —CF$_3$;

$R^9$ is hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —NO$_2$, halogen, —NHCO$_2$R$^{13}$, —NHSO$_2$R$^{13}$, —NR$^{14}$R$^{15}$,

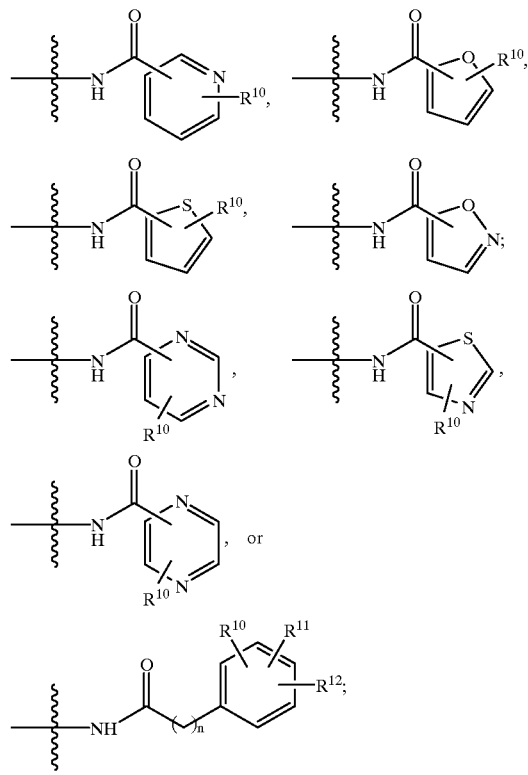

$R^{10}$, $R^{11}$, and $R^{12}$ are each, independently, hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —NO$_2$, halogen, acyl of 2–7 carbon atoms, perfluoroacyl of 2–7 carbon atoms, or benzoyl, wherein the phenyl moiety of the benzoyl group is optionally mono-, di-, or tri-substituted with alkyl of 1–6 carbon atoms, alkoxy of 1–6 carbon atoms, —CN, —NO$_2$, halogen, or —CF$_3$;

$R^{13}$ is alkyl of 1–6 carbon atoms, perfluoroalkyl of 1–6 carbon atoms, phenyl or phenyl substituted with halogen;

$R^{14}$ and $R^{15}$ are each, independently, hydrogen, alkyl of 1–6 carbon atoms, perfluoroalkyl of 1–6 carbon atoms, acyl of 2–7 carbon atoms, perfluoroacyl of 2–7 carbon atoms;

n=0–3;

or a pharmaceutically acceptable salt thereof.

25. A pharmaceutical composition which comprises a compound of formula I having the structure

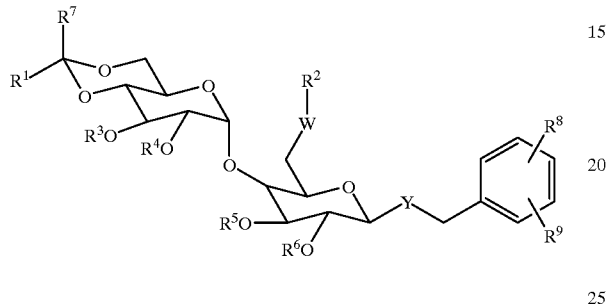

wherein

W is S, SO, $SO_2$, NR;

Y is O, S, NR, or $CH_2$;

R is hydrogen or alkyl of 1–6 carbon atoms, perfluoroalkyl of 1–6 carbon atoms, acyl of 2–7 carbon atoms, perfluoroacyl of 2–7 carbon atoms;

$R^1$ and $R^7$ are each, independently, alkyl of 1–6 carbon atoms, perfluoroalkyl of 1–6 carbon atoms, haloalkyl of 1–6 carbon atoms, nitroalkyl of 1–6 carbon atoms, cyanoalkyl of 1–6 carbon atoms, alkoxyalkyl of 2–12 carbon atoms, nitriloalkyl of 1–6 carbon atoms, phenyl mono-, di-, or tri-substituted with $R^8$, phenylalkyl of 7–10 carbon atoms, wherein the phenyl ring is mono-, di-, or tri-substituted with $R^8$, pyridyl substituted with $R^8$, furyl substituted with $R^8$, thienyl substituted with $R^8$, and thiazolyl substituted with $R^8$;

$R^2$ is hydrogen,

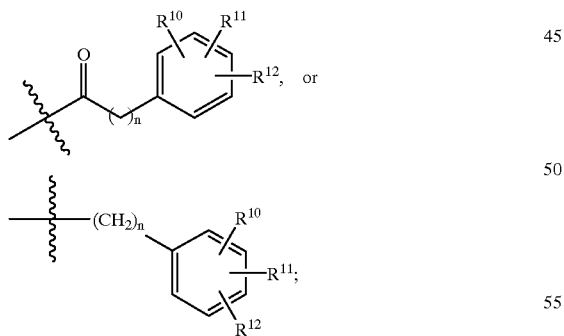

$R^3$, $R^4$, $R^5$, and $R^6$ are each, independently, hydrogen, acyl of 2–7 carbon atoms, perfluoroacyl of 2–7 carbon atoms, alkyl of 1–6 carbon atoms, perfluoroalkyl of 1–6 carbon atoms, benzyl, wherein the phenyl moiety is mono-, di-, or tri-substituted with $R^8$, benzoyl, wherein the phenyl moiety is mono-, di-, or tri-substituted with $R^8$;

$R^8$ is hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —$NO_2$, halogen, or —$CF_3$;

$R^9$ is hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —$NO_2$, halogen, —$NHCO_2R^{13}$, —$NHSO_2R^{13}$, —$NR^{14}R^{15}$,

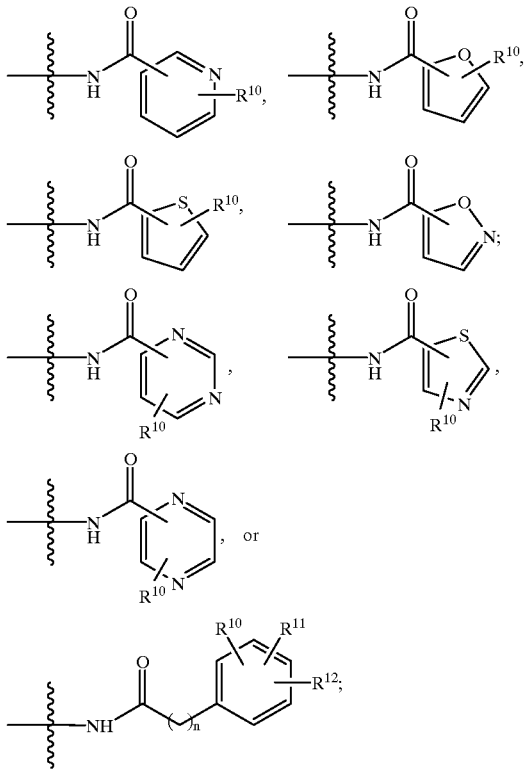

$R^{10}$, $R^{11}$, and $R^{12}$, are each, independently, hydrogen, alkyl of 1–6 carbon atoms, perfluoroalkyl of 1–6 carbon atoms, alkoxy of 1–6 carbon atoms, perfluoroalkoxy of 1–6 carbon atoms, phenyl, —CN, —$NO_2$, halogen, acyl of 2–7 carbon atoms, perfluoroacyl of 2–7 carbon atoms, or benzoyl, wherein the phenyl moiety of the benzoyl group is optionally mono-, di-, or tri-substituted with alkyl of 1–6 carbon atoms, alkoxy of 1–6 carbon atoms, —CN, —$NO_2$, halogen, or —$CF_3$;

$R^{13}$ is alkyl of 1–6 carbon atoms, perfluoroalkyl of 1–6 carbon atoms, phenyl or phenyl substituted with halogen;

$R^{14}$ and $R^{15}$ are each, independently, hydrogen, alkyl of 1–6 carbon atoms, perfluoroalkyl of 1–6 carbon atoms, acyl of 2–7 carbon atoms, perfluoroacyl of 2–7 carbon atoms;

n=0–3;

or a pharmaceutically acceptable salt thereof, and a pharmaceutical carrier.

* * * * *